United States Patent
Demopulos et al.

[11] Patent Number: 6,080,192
[45] Date of Patent: *Jun. 27, 2000

[54] TENDON AND LIGAMENT REPAIR SYSTEM

[75] Inventors: Gregory A. Demopulos, Mercer Island, Wash.; Stephen A. Yencho, Stanford, Calif.; David A. Herrin, Seattle, Wash.; Neil G. McIlvaine, Seattle, Wash.; Michael D. Nelson, Seattle, Wash.; Milton R. Sigelmann, Seattle, Wash.; Jose T. V. de Castro, Newton, Mass.; George Selecman, Marblehead, Mass.; John Collins, Ipswich, Mass.; Imraan Aziz, Stanford, Calif.; Gorm Bressner, Providence, R.I.

[73] Assignee: Omeros Medical Systems, Inc., Seattle, Wash.

[*] Notice: This patent is subject to a terminal disclaimer.

[21] Appl. No.: 09/086,126

[22] Filed: May 28, 1998

Related U.S. Application Data

[63] Continuation of application No. 08/567,311, Dec. 4, 1995, Pat. No. 5,800,544, which is a continuation-in-part of application No. 08/349,358, Dec. 2, 1994, abandoned.

[51] Int. Cl.[7] .................................................. A61F 2/08
[52] U.S. Cl. ............................... 623/13; 623/11; 606/53; 606/72
[58] Field of Search .......................... 623/11, 13; 606/53, 606/72

[56] References Cited

U.S. PATENT DOCUMENTS

| | | |
|---|---|---|
| 3,124,136 | 3/1964 | Usher . |
| 3,176,316 | 4/1965 | Bodell . |
| 3,545,008 | 12/1970 | Bader, Jr. . |
| 3,646,615 | 3/1972 | Ness . |
| 3,805,300 | 4/1974 | Tascon-Alonso et al. . |
| 3,833,002 | 9/1974 | Palma . |
| 3,842,441 | 10/1974 | Kaiser . |

(List continued on next page.)

FOREIGN PATENT DOCUMENTS

WO 96/16612  6/1996  WIPO .

OTHER PUBLICATIONS

Boynton, M.D. and Fadale, P.D., The basic science of anterior cruciate ligament surgery. *Orthop. Rev.* 22:673–679 (1993).

Hoffmann, M.W. et al., Repair and reconstruction of the anterior cruciate ligament by the "sandwich technique", *Arch. Orthop. Trauma Surg.*, 112:113–120 (1993).

Lazovic, D. and Messner, K., Collagen repair not improved by fibrin adhesive, *Acta Orthop. Scand.*, 64:583–586 (1993).

Lyon, R.M. et al., Ultrastructural differences between the cells of the medial collateral and the anterior cruciate ligaments, *Clin. Orthop.*, 279–286 (1991).

Nogalski, M.P. and Bach, B.R., Jr., A review of early anterior cruciate ligament surgical repair or reconstruction, *Orthop.*, 2:2:1213–1223 (1993).

(List continued on next page.)

*Primary Examiner*—Paul B. Prebilic
*Attorney, Agent, or Firm*—Christensen O'Connor Johnson & Kindness PLLC

[57] ABSTRACT

The damaged portion of an injured tendon or ligament (C) ("connective cord") is inserted into a thin, hollow sleeve (100, 110, 120, 130, 140, 160, 180, 200, 240, 260, 270, 300, 390, generically designated "S") and is connected to the sleeve (S) such that the cord-sleeve combination can immediately withstand normal tensile forces. The interconnection can be mechanical, such as by pins (22, 22',148, 150, 164, 188, 190, 206, 206', 210, 226, 230, 238, 239, 266, 286, 308) extending through the sleeve (S) and cord (C). The sleeve (S) can be bioabsorbable over a sufficiently long period of time that the cord (C) is healed by the time the sleeve (S) is absorbed.

56 Claims, 19 Drawing Sheets

U.S. PATENT DOCUMENTS

| | | |
|---|---|---|
| 3,987,497 | 10/1976 | Stoy et al. . |
| 3,992,725 | 11/1976 | Homsy . |
| 4,246,660 | 1/1981 | Wevers . |
| 4,414,967 | 11/1983 | Shapiro . |
| 4,469,101 | 9/1984 | Coleman et al. . |
| 4,501,029 | 2/1985 | McMinn . |
| 4,512,038 | 4/1985 | Alexander et al. . |
| 4,534,349 | 8/1985 | Barrows . |
| 4,535,763 | 8/1985 | Jaquet . |
| 4,610,688 | 9/1986 | Silvestrini et al. . |
| 4,643,734 | 2/1987 | Lin . |
| 4,755,183 | 7/1988 | Kenna . |
| 4,776,851 | 10/1988 | Bruchman et al. . |
| 4,828,562 | 5/1989 | Kenna ................................... 606/72 |
| 4,870,957 | 10/1989 | Goble et al. . |
| 4,950,271 | 8/1990 | Lewis et al. . |
| 4,960,420 | 10/1990 | Goble et al. . |
| 4,979,956 | 12/1990 | Silvestrini . |
| 4,997,433 | 3/1991 | Goble et al. . |
| 5,002,574 | 3/1991 | May et al. . |
| 5,011,486 | 4/1991 | Aebischer et al. . |
| 5,061,281 | 10/1991 | Mares et al. . |
| 5,061,283 | 10/1991 | Silvestrini . |
| 5,108,433 | 4/1992 | May et al. . |
| 5,122,151 | 6/1992 | de Medinaceli . |
| 5,147,362 | 9/1992 | Goble . |
| 5,151,104 | 9/1992 | Kenna . |
| 5,250,055 | 10/1993 | Moore et al. . |
| 5,306,301 | 4/1994 | Graf et al. . |
| 5,314,427 | 5/1994 | Goble et al. . |
| 5,374,269 | 12/1994 | Rosenberg . |
| 5,425,766 | 6/1995 | Bowald . |
| 5,458,601 | 10/1995 | Young, Jr. et al. . |
| 5,458,636 | 10/1995 | Brancato . |
| 5,645,589 | 7/1997 | Li ................................. 623/13 |
| 5,723,008 | 3/1998 | Gordon . |
| 5,766,250 | 6/1998 | Chervitz et al. ................. 623/13 |
| 5,800,544 | 9/1998 | Demopulos et al. ............. 623/13 |
| 5,931,840 | 8/1999 | Goble et al. ..................... 623/13 |
| 5,931,869 | 8/1999 | Boucher et al. ................. 623/13 |

OTHER PUBLICATIONS

Paessler, H.H., et al., Augmented repair and early mobilization of acute anterior cruciate ligament injuries, *Am. J. Sports Med.*, 20:667–674 (1992).

Sgaglione, N.A., et al., Primary repair with semitendinosus tendon augmentation of acute anterior cruciate ligament injuries, *Am. J. Sports Med.*, 18:64–73 (1990).

Sherman, M.F., et al., The long–term followup of primary anterior cruciate ligament repair: Defining a rationale for augmentation, *Am. J. Sports Med.*, 19:243–255 (1991).

Wiig, M.E., et al., The early effect of high molecular weight hyaluronan (hyaluronic acid) on anterior cruciate ligament healing: An experimental study in rabbits, *J. Orthop. Res.*, 8:425–434 (1990).

Flexor tendon repair: Indiana Method,*The Indiana Hand Center Newsletter*, 1:1–20 (1993).

Ketchum, L.D. Primary tendon healing: A review, *J. Hand Surg.*, 2(6):428–435 (1977).

Richards, H.J., Repair and healing of the divided digital flexor tendon, *The British Journal of Accident Surgery*, 12:1–12.

Furlow, L.T., Jr., The role of tendon tissues in tendon healing, 57:39–49 (1976).

Gelberman, R.H., et al., Influences of flexor sheath continuity and early motion on tendon healing in dogs, *J. Hand Surg.*, 15A:69–77 (1990).

Gelberman, R.H., et al., Fibroblast chemotaxis after tendon repair, *J. Hand Surg.*, 16A:686–693 (1991).

Gelberman, R.H., et al., The revascularization of healing flexor tendons in the digital sheath, *J. Bone and Joint Surg., Inc.*, 73A:868–881 (1991).

Becker, H., Primary repair of flexor tendons in the hand without immobilization—Preliminary report, *The Hand*, 10:37–47 (1978).

Goodship, A.E., et al., The development of tissue around various prosthetic implants used as replacements for ligaments and tendons, *Clin. Ortho. and Related Res.*, 196:61–68 (1985).

Engebretsen, L., et al., A prospective, randomized study of three surgical techniques for treatment of acute ruptures of the anterior curciate ligament, *Am. J. Sports Med.*, 18:585–590 (1990).

Kennedy, J.C., et al., Presidential address: Intraarticular replacement in the anterior cruciate ligament–deficient knee, *Am. J. Sports Med.*, 8:1, 7–8 (1980).

Strover, A.E., and Firer, P., The use of carbon fiber implants in anterior cruciate ligament surgery, *Clin. Ortho. and Related Res.*, 196:88–89 (1985).

Cross, M.J., et al., Acute repair of injury to the anterior cruciate ligament. A long–term followup, *Am. J. Sports Med.*, 21:128–131 (1993).

Manske, P.R., The flexor tendon, *Orthopedics*, 10:1733–1741 (1987).

Pring, D.J., et al., The mechanical properties of human flexor tendons in relation to artifical tendons, *J. Hand Surg.*, 10B:331–336 (1985).

Doyle, J.R., Anatomy of the finger flexor tendon sheath and pulley system, *J. Hand Surg.*, 13A:473–484 (1988).

Strum, G.M. and Larson, R.L., Clinical experience and early results of carbon fiber augmentaion of anterior cruciate reconstruction of the knee, *Corr.*, 196:124–138 (1985).

Park, J.P., et al., A high–strength dacron augmentation for cruicate ligament reconstruction, *Corr.*, 196:175–185 (1985).

McPherson, G.K., et al., Experiment mechanical and histologic evaluation of the Kennedy ligament augmentation device, *Corr.*, 196:186–195 (1985).

Bolton, C.W. and Bruchman, W.C., The GORE–TEX™ expanded polytetrafluoroethylene prosthetic ligament: An in vitro and in vivo evaluation, *Corr.*, 196:202–213 (1985).

Silfverskold, K.L., et al., Two new methods of tendon repair: An in vitr evaluation of tensile strength and gap formation, *J. Hand Surg.*, 18A:58–65 (1993).

Dodds, J.A., et al., Anatomy of the anterior cruciate ligament: A blueprint for repair and reconstruction, *J. Arthroscopic and Related Surgery*, 10(2):132–139 (1994).

Radford, W.J.P., et al., Immediate Strength After Suture Of A Torn Anterior Cruciate Ligament, *J. of Bone and Joint Surgery*, 76–B:480–483 (1994).

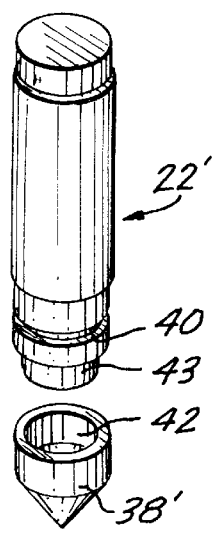
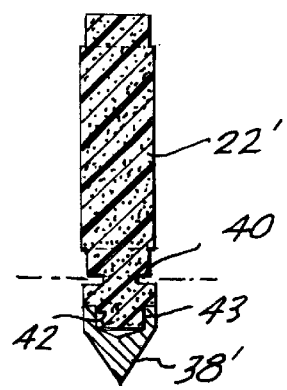
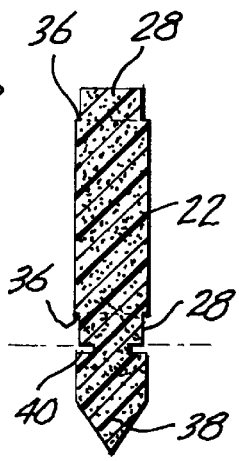
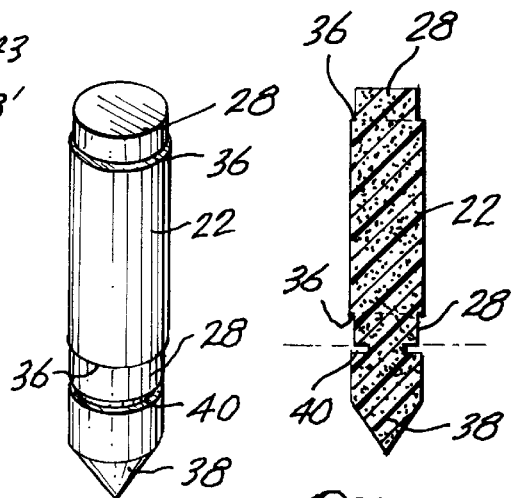
Fig. 7.  Fig. 8.  Fig. 5.  Fig. 6.
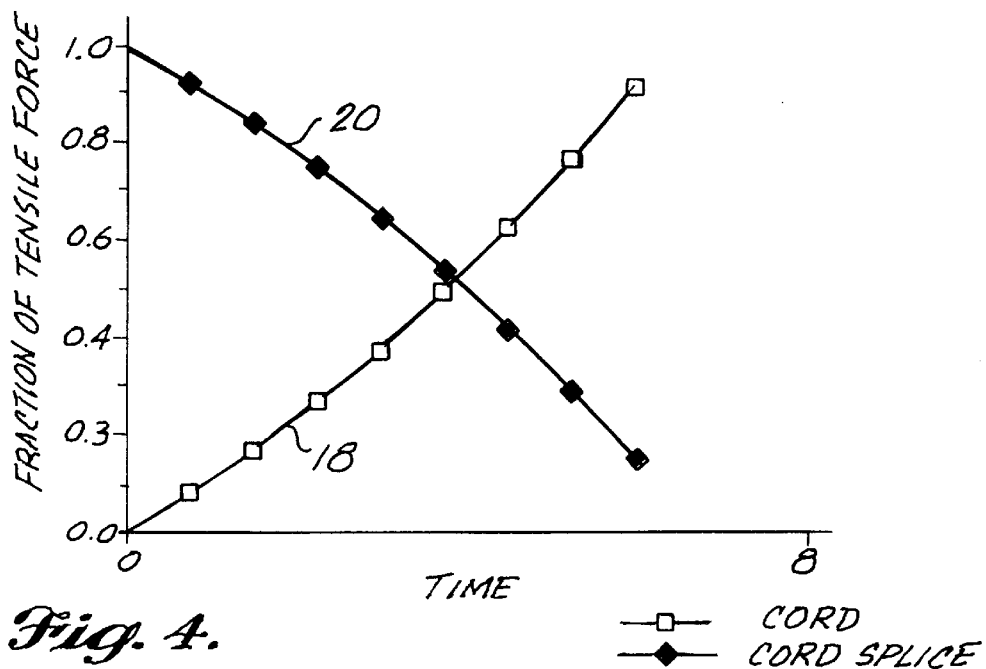
Fig. 4.

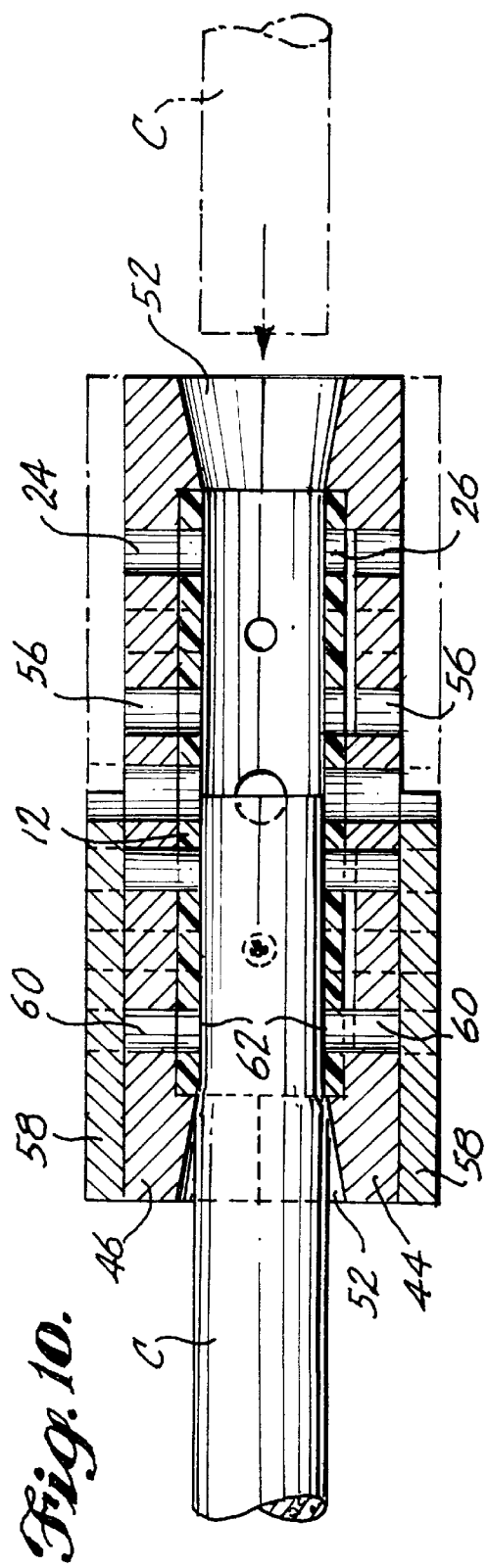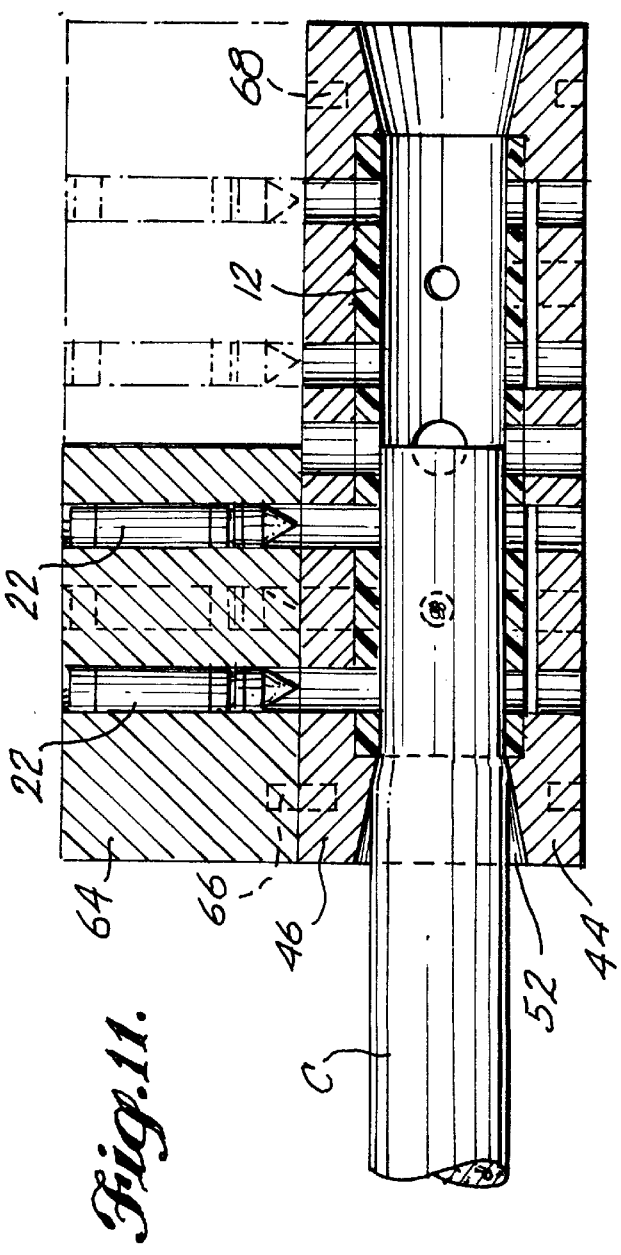

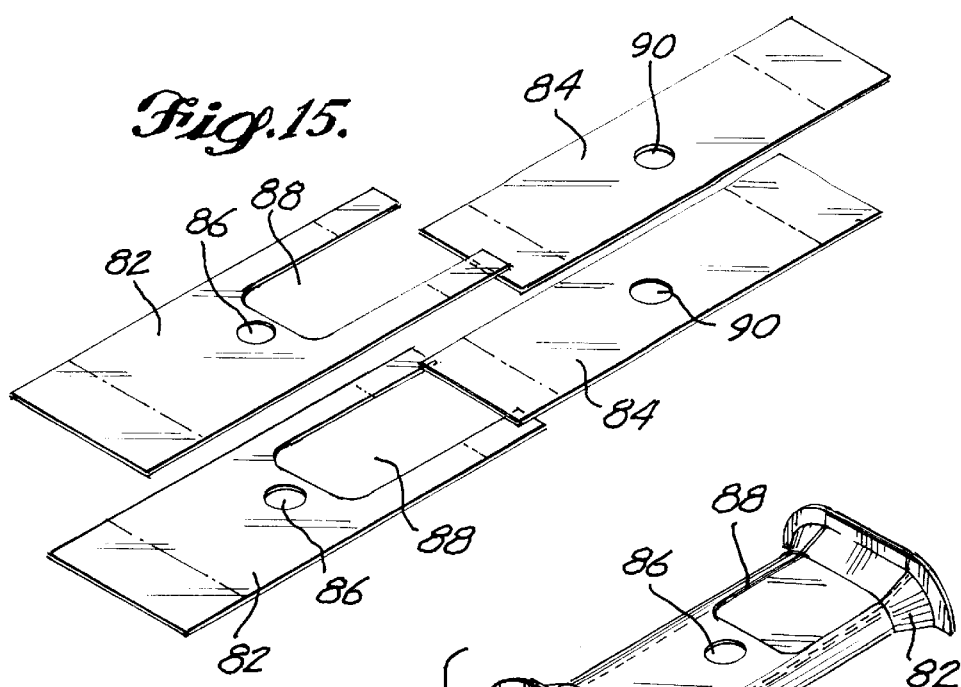
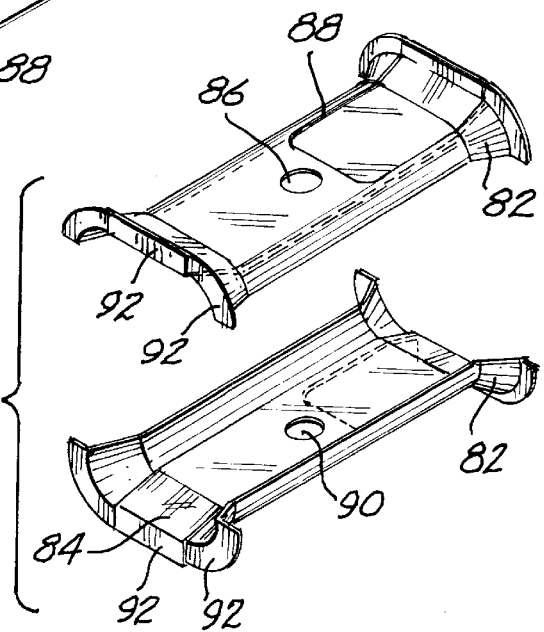
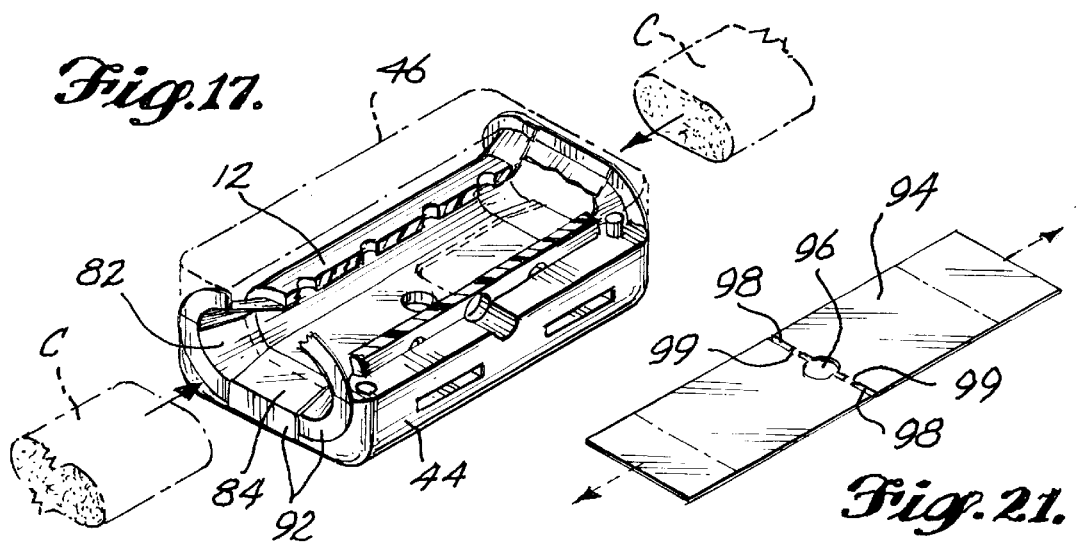

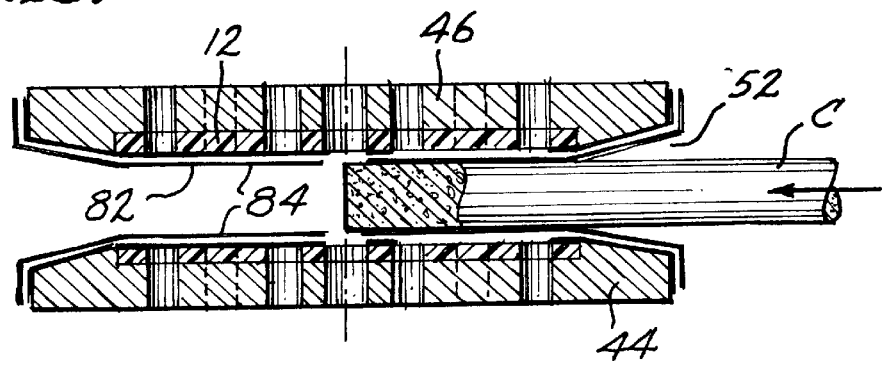
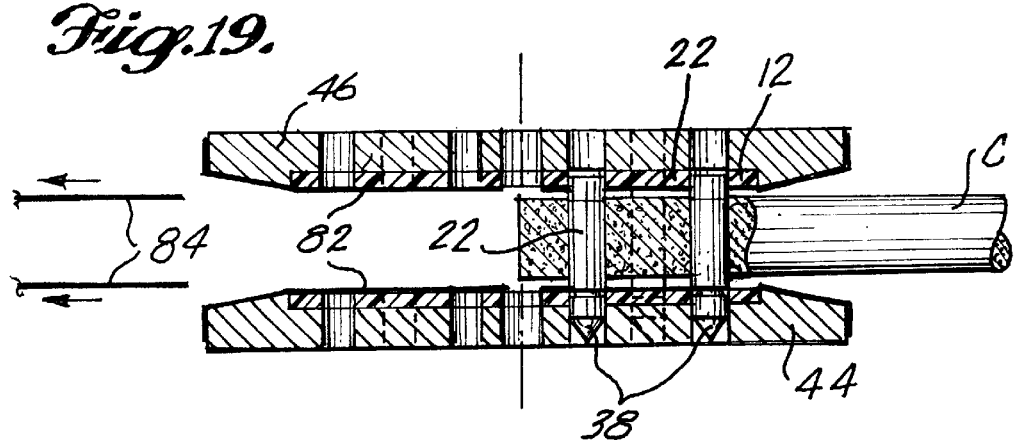
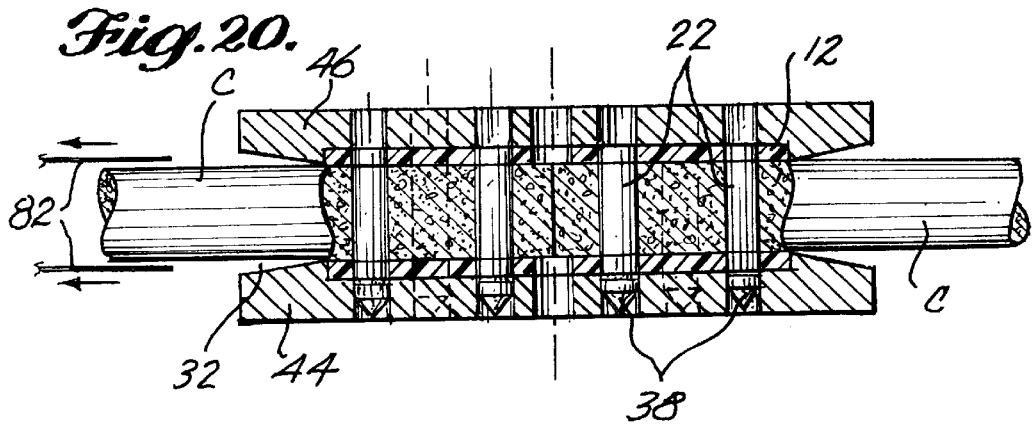

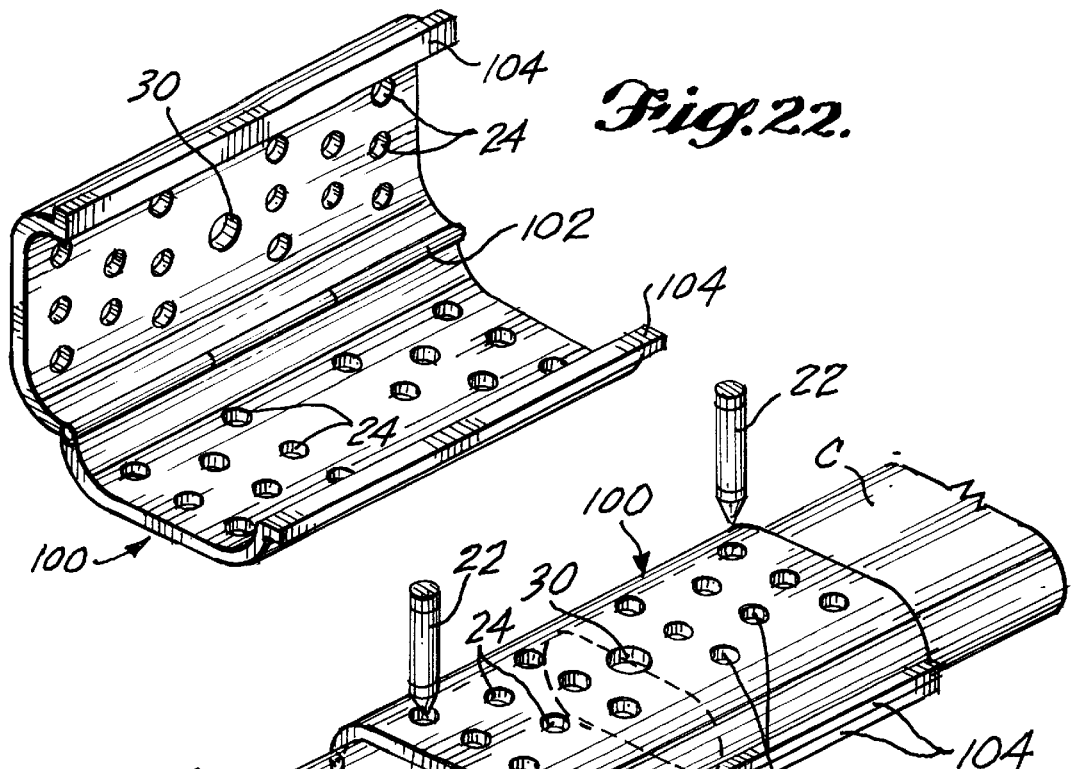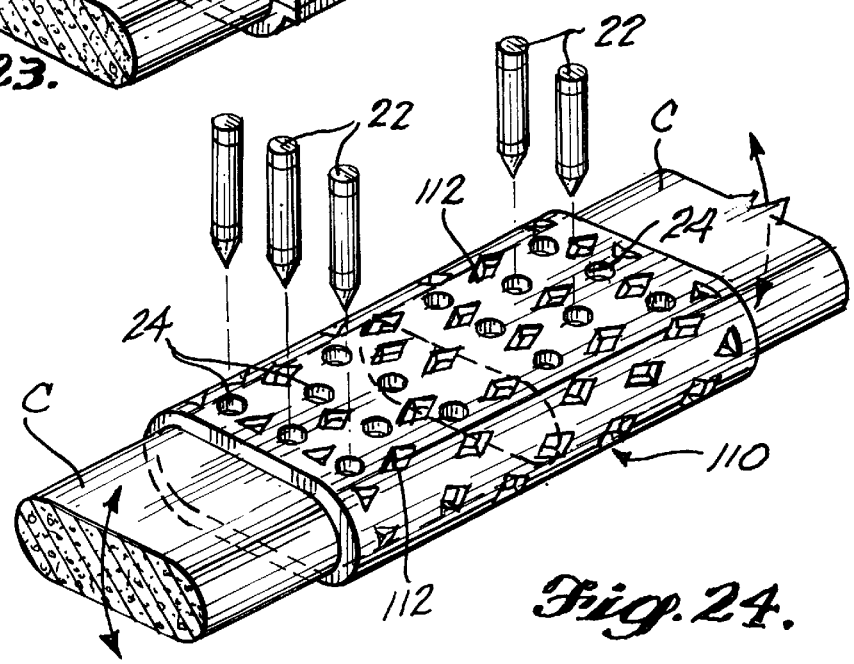

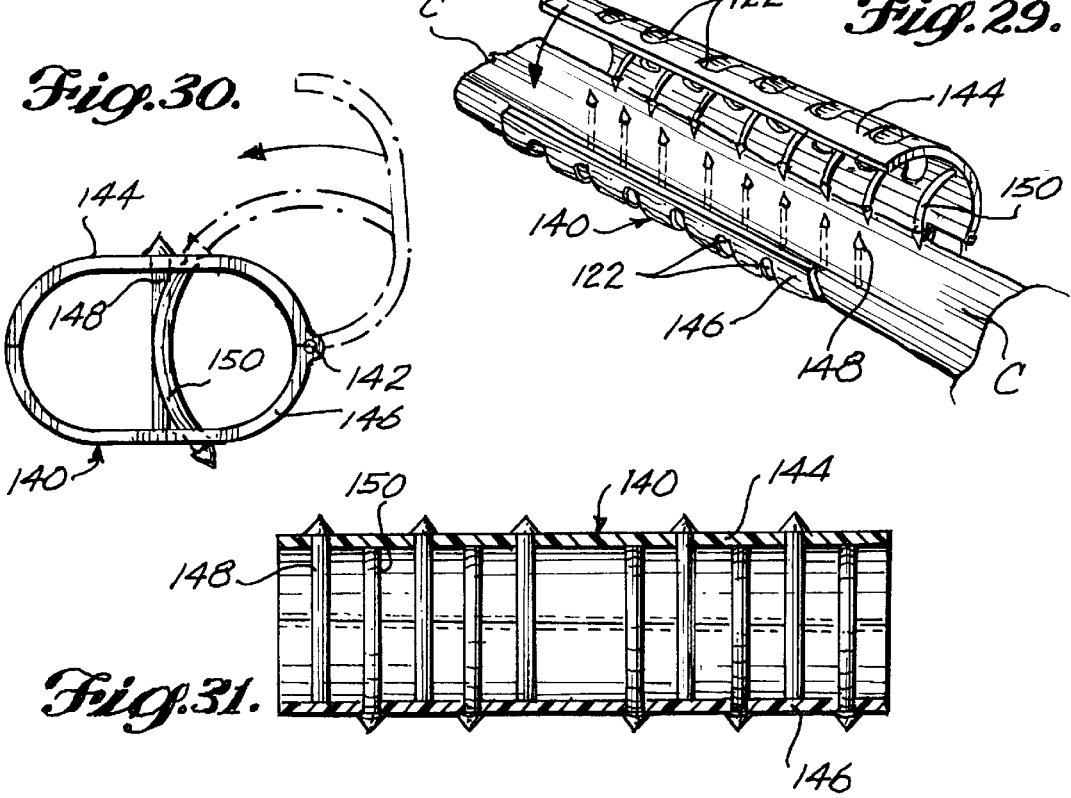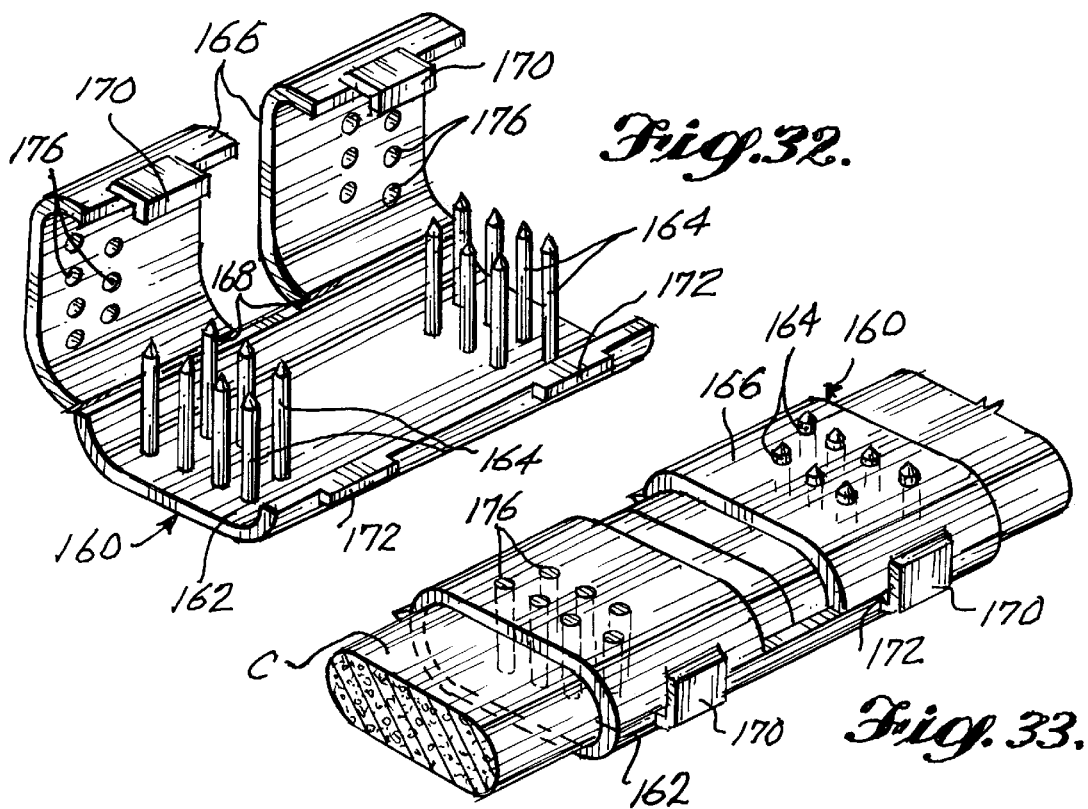

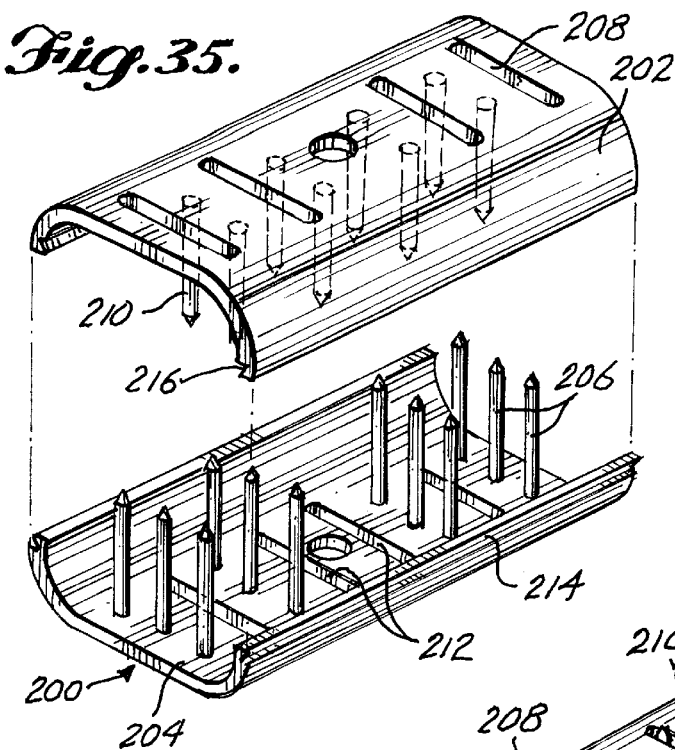
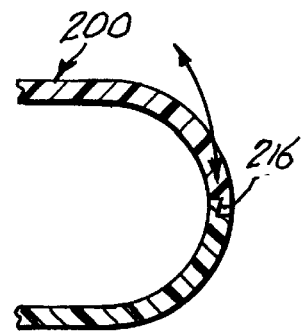
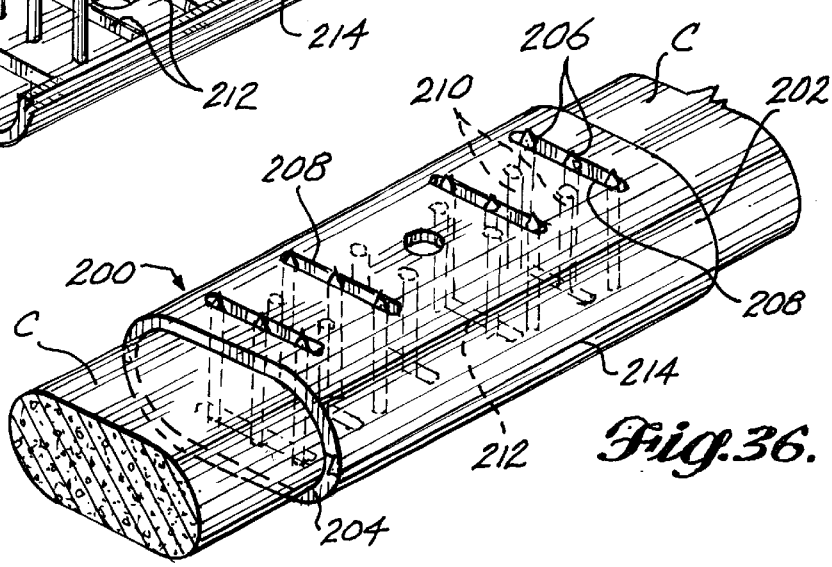
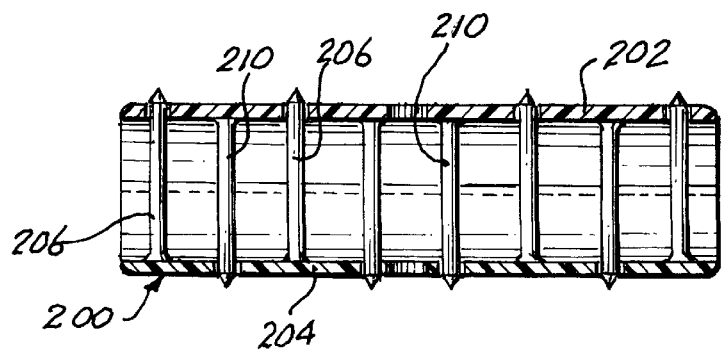

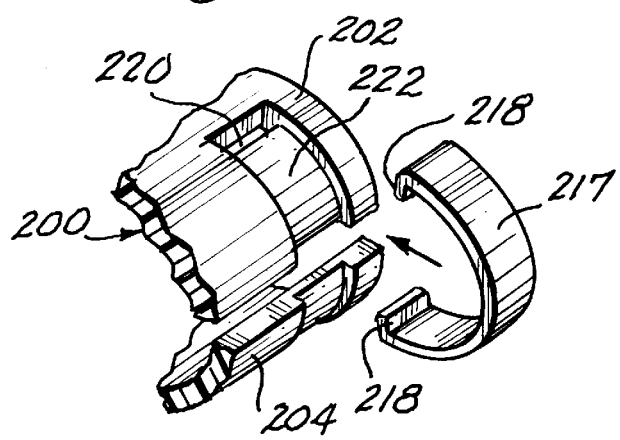
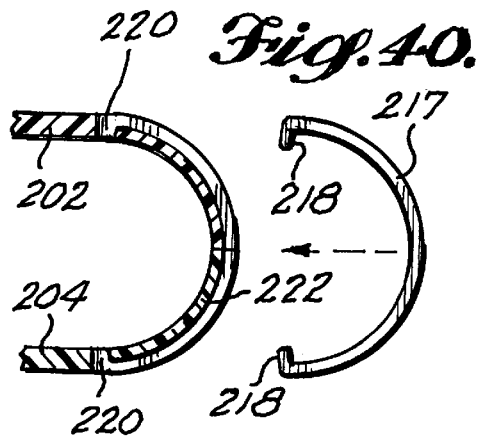
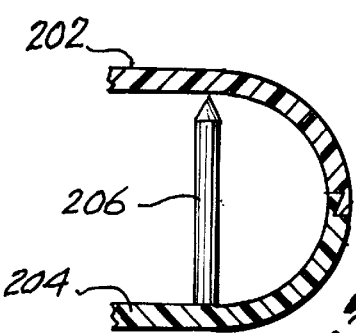
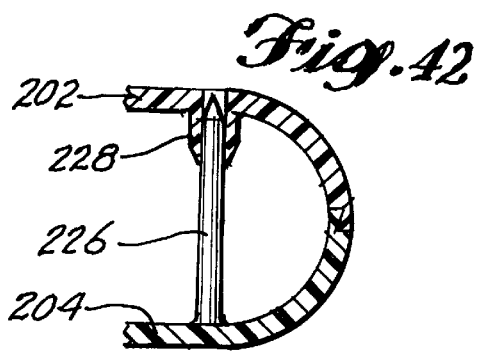
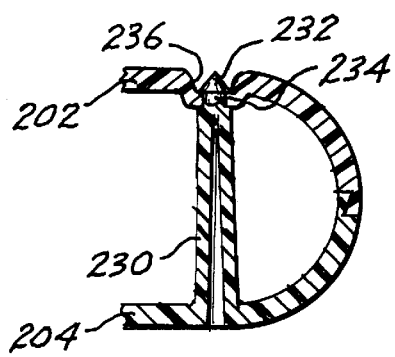
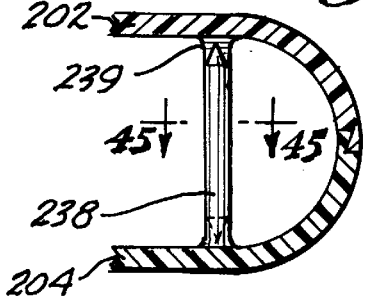

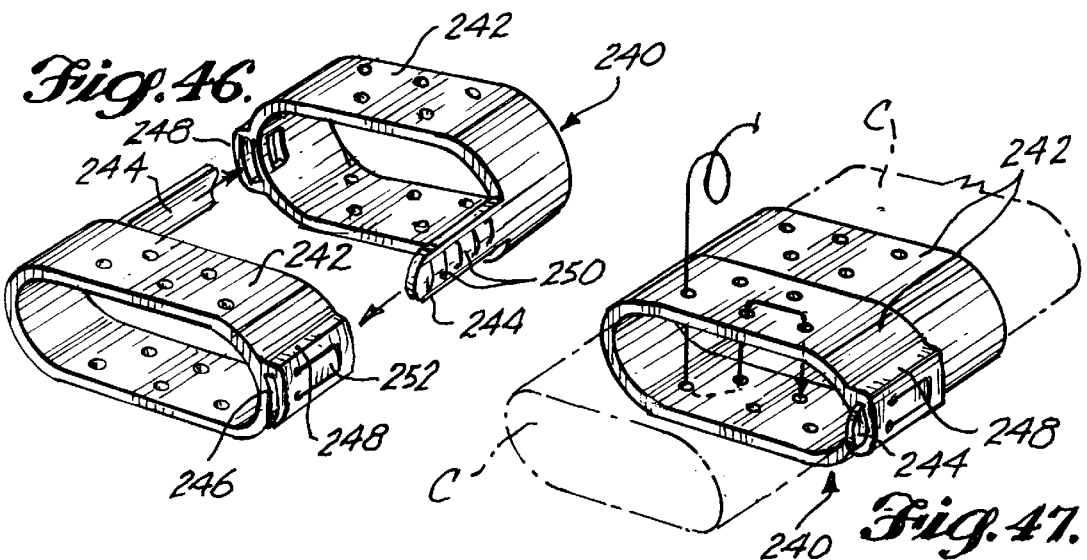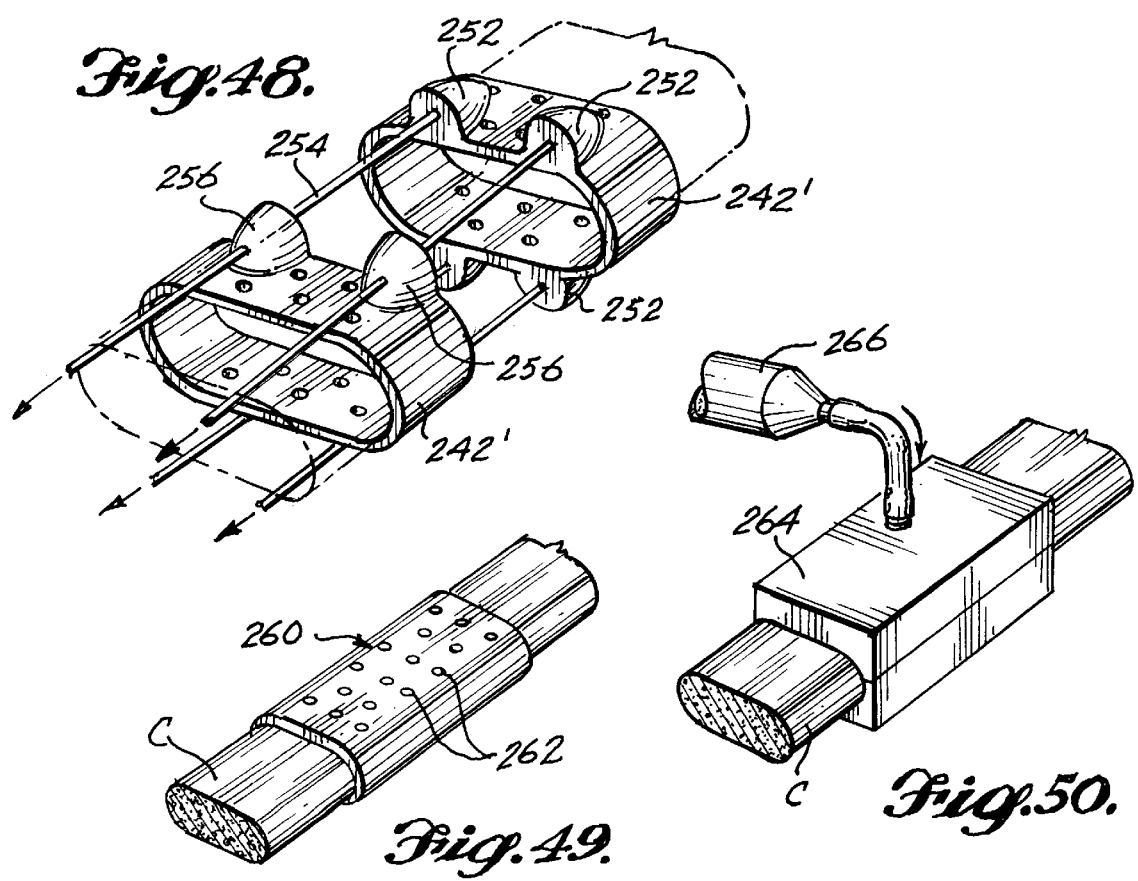

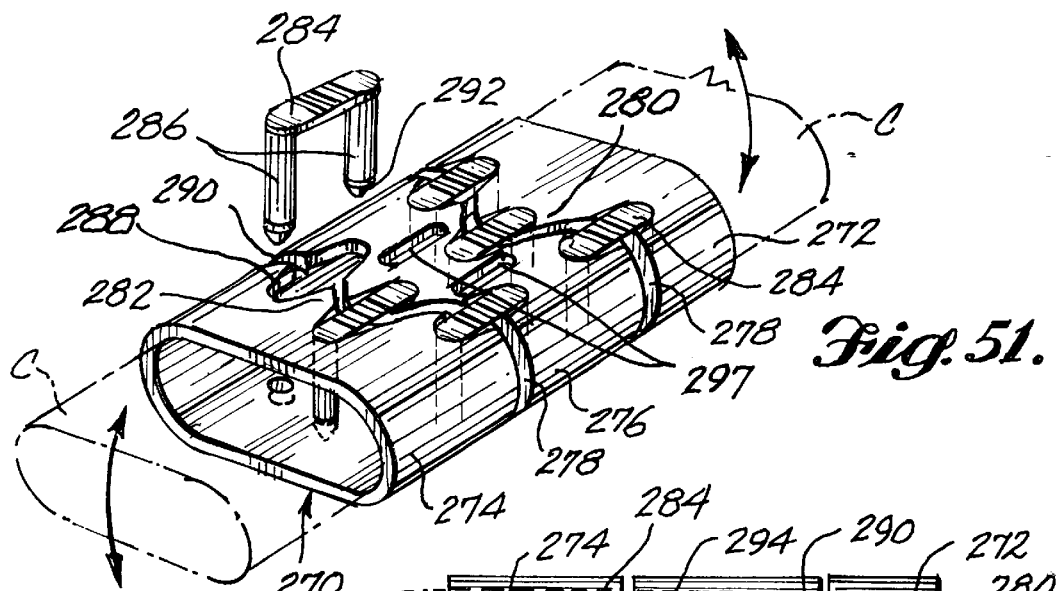
Fig. 51.
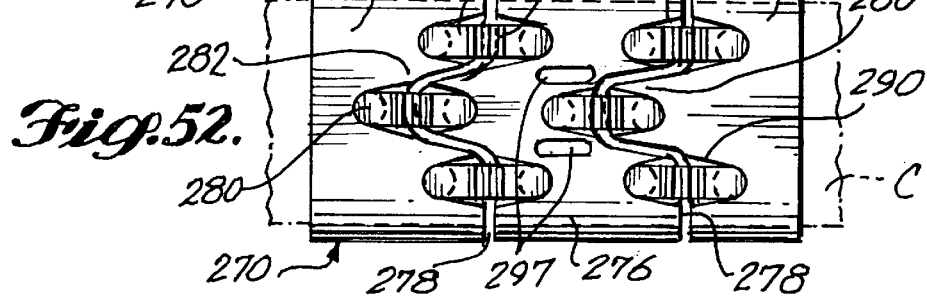
Fig. 52.
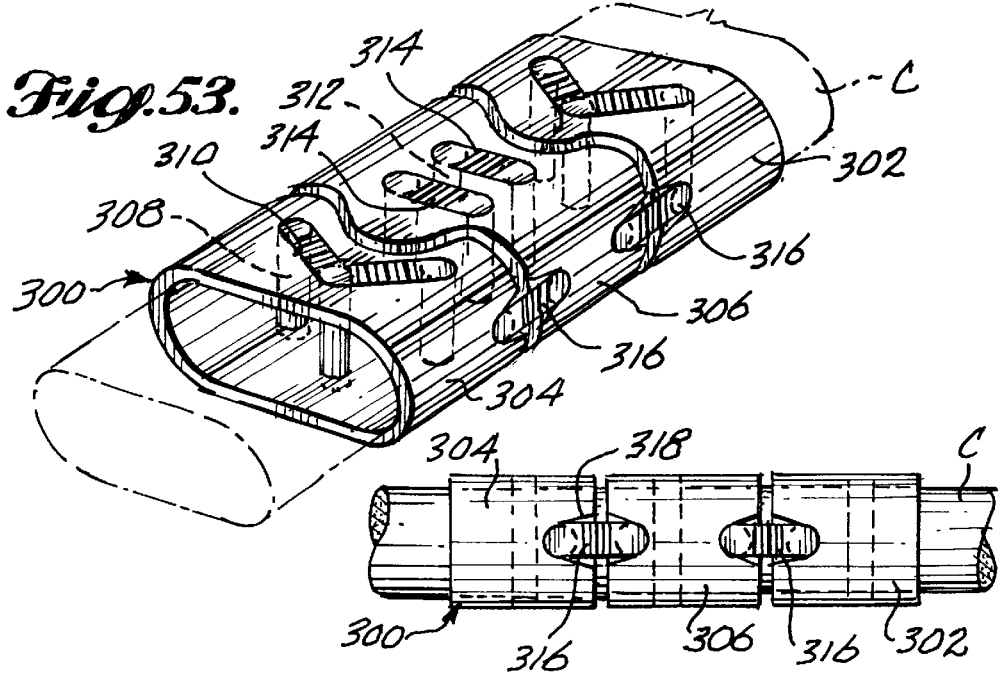
Fig. 53.
Fig. 54.

TENDON AND LIGAMENT REPAIR SYSTEM

RELATION TO PRIOR APPLICATION

This application is a continuation of U.S. patent application Ser. No. 08/567,311, filed on Dec. 4, 1995, titled "TENDON AND LIGAMENT REPAIR SYSTEM," now U.S. Pat. No. 5,800,544 which is a continuation-in-part of U.S. patent application Ser. No. 08/349,358, filed on Dec. 2, 1994, titled "TENDON AND LIGAMENT SPLICE," now abandoned and which are expressly incorporated by reference herein.

FIELD OF THE INVENTION

The present invention relates to a system for repairing lacerated or severed fibrous connective tissue, referred to herein as "connective cords" or "cords," particularly tendons and ligaments.

BACKGROUND OF THE INVENTION

Repair techniques for lacerated or severed tendons and ligaments ("connective cords" or "cords") vary widely depending on the nature of the injury and the particular cord affected. There are large differences in the extent to which access can be obtained in the least obtrusive manner, in the amount of cord excursion, in the surrounding environment, in the stresses to which different cords are normally subjected, and in the healing characteristics of different cords. In addition, often there is no consensus of the overall best way to repair a given cord. Examples of often injured cords having different accepted repair techniques are flexor tendons of the hand and the anterior cruciate ligament (ACL) of the knee.

For example, repair of a long flexor tendon that has been severed is typically achieved by suturing the severed tendon ends face-to-face. Historically, the joints across which the tendon acts were immobilized for from three to eight weeks to protect the tendon while it healed, because a freshly sutured tendon can withstand only a fraction of the tensile force to which a healthy tendon is subjected during normal use. Immobilization results in scarring and adhesion formation along the length of the tendon. Range of motion is adversely affected, particularly in the case of flexor tendons which normally glide smoothly through and over the unique system of tendon tunnels and pulleys of the hand. Nevertheless, it was thought that fibroblastic ingrowth was required in order for the tendon to heal, such that immobilization and the resulting decreased range of motion were considered necessary evils in order for effective healing to take place. More recently it has been discovered that flexor tendons have an intrinsic capacity to heal and that limited motion will actually expedite healing. Still, exercises must be carefully planned and carried out due to the weakness of the sutured repair. In early stages of healing, restricted active exercises may be used, followed by some passive and active exercises in later stages. The affected joints are most often partially immobilized to prevent inadvertent application of excess force.

In the case of an anterior cruciate ligament (connecting the bottom of the femur and the top of the tibia) the stresses resulting from applied forces are much greater, there is less interaction with surrounding tissue and bone, the excursion of the cord is less, and the healing tendencies are vastly different. Despite numerous studies, there still is no universally accepted repair procedure, and prevailing procedures are difficult and intricate. The current "standard of care" remains the reconstruction of the ACL using a bone-tendon-bone autograft (i.e., harvested from the patient). However, there are multiple problems with bone-tendon-bone grafting. (1) The intact ACL possesses important mechanoreceptive and proprioceptive capabilities. Graft reconstruction sacrifices these capabilities. (2) Autografting involves considerable donor site morbidity. (3) To avoid donor site morbidity, occasionally a cadaveric graft is used. This carries the risk of disease transmission.

These problems with ACL reconstruction have led to renewed interest in primary repair of the ACL. In the case of primary repair without augmentation, small bores are drilled in the adjacent bones approximately at the anatomically correct sites for normal connection of the ACL. Multiple loops of suture are used for reconnecting the ligamentous stumps to the bone. Several loops of permanent suture can provide an initial strong repair. However, over time the strength of the repaired ACL often decreases, which is indicative of a failure in the healing process. In general, it is now accepted that healing tendencies of the intra-articular ACL are poor, particularly when compared to the neighboring extra-articular medial collateral ligament which heals readily.

Failure or long-term weakening of ACL primary repair has led to techniques for "augmenting" a primary repair. These can involve suturing biological material, such as a section of patellar tendon, across a repair site, and the use of artificial augmenting strips or sheaths which typically have been flexible and fibrous in the hope that healing of the ACL will be promoted, rather than being inhibited by, the close proximity of an artificial "shield." Strips or bands of Dacron, polyethylene or carbon fiber have had their opposite ends stapled or otherwise anchored to the adjacent bones to provide the primary or secondary support for the "healing" ACL.

SUMMARY OF THE INVENTION

The present invention provides a system for repair of injured connective cords by enclosing the affected cord ends in a hollow sleeve and securing the adjacent end portions of the cord inside the sleeve. In one embodiment, the sleeve has a central observation port for viewing the cord-end interface, and an internal groove or grooves to allow vascular flow to the cord. Holes along the axis of the sleeve also permit diffusion of synovial fluid or other normal healing agents. The cord end portions can be secured to the sleeve mechanically, preferably by several pins at each side. The pins can be arranged in rows with pins of adjacent rows staggered and with adjacent pins spaced apart sufficiently to prevent inordinate localized stresses from being applied to the tissue when the tendon is tensioned.

In the case of a tendon that normally glides along adjacent tissue and/or bone, it is important that the sleeve be as thin as possible so as not to interfere with the gliding motion. In addition, normal gliding may be enhanced by forming the sleeve in an oval shape with a horizontal major axis much longer than a vertical minor axis. The mechanical interconnection of the cord ends and the sleeve preferably is sufficiently strong that immobilization is not required. Strengthening and healing promoting exercises can begin almost immediately.

The sleeve and any mechanical connection components can be bioabsorbable. The period of bioabsorbability is selected based on the healing characteristics of the affected connective cord. Ideally, the sleeve and mechanical connection components will remain sufficiently strong over time such that the overall force that the repaired connective cord can withstand always is at least as great as the force to which it is normally subjected. For example, in the early stages when the cord itself has essentially no resistance to separation, the sleeve and connection components will withstand a strong tensile force. As the connective cord heals and is capable of withstanding substantial force on its own, the partially absorbed sleeve and connection components need not withstand as much force as at the outset.

The connection pins can be formed with sharp tips for driving through the sleeve and enclosed cord end portions. The pins can extend between aligned holes in the sleeve. The sharpened end portions of the pins can be cut or broken off following insertion. Preferably, the opposite ends of the pins lie flush with the outer periphery of the sleeve when the repair is complete. In addition, the pins can be formed with interior shoulders to engage against the inner periphery of the sleeve for reliably holding the pins in position.

Manipulation of the sleeve and insertion of the cord ends can be aided by positioning the sleeve in a broader, outer ferrule having inclined ramps or entrances leading to the interior of the sleeve. Resistance to cord insertion can be lessened by filling the pin holes with removable plugs, or by covering the holes at the inside with removable foil strips. The plugs or strips are removed after tendon insertion to provide access to the holes for driving the pins therethrough. The pins can be supplied in cartridges, with a special tool being provided for driving several of the pins through the sleeve simultaneously. The ferrules can have transverse slots aligned with the periphery of the sleeve for receiving a blade to cut off the sharpened pin ends flush with the outer periphery of the sleeve.

The sleeve can be a unitary enclosure for the connective cord, i.e., having a continuous peripheral wall, or it can be formed with a hinge or hinges along one longitudinal side for opening and closing in clamshell fashion, or it can be formed of separate pieces. In the case of a hinged or multiple piece sleeve, the pins can be formed integrally with the sleeve for penetrating the connective cord as the sleeve parts are brought together. The sleeve can be designed in such a way as to bend about a transverse axis, and may have a smooth covering for normal excursion without snagging or abrading adjacent tissue. One severed end of a connective cord can be secured in a sleeve in accordance with the present invention, with the sleeve being adapted to be secured to a bone, particularly in the case of an ACL severed close to its normal connection to the tibia or femur.

BRIEF DESCRIPTION OF THE DRAWINGS

The foregoing aspects and many of the attendant advantages of this invention will become more readily appreciated as the same becomes better understood by reference to the following detailed description, when taken in conjunction with the accompanying drawings, wherein:

FIG. 4 is a graph illustrating the relative strengths of a splice in accordance with the present invention and a healing connective cord over time;

FIG. 5 is a top perspective of a component of the splice in accordance with the present invention, namely, a connection pin, and FIG. 6 is a longitudinal section thereof;

FIG. 7 is a top perspective of an alternative connection pin, with parts shown in exploded relationship, and FIG. 8 is a longitudinal section thereof with parts assembled;

FIGS. 10, 11, 12 and 13 are corresponding longitudinal vertical sections of a splice in accordance with the present invention, illustrating different steps in the procedure of cord repair;

FIG. 15 is a top perspective of optional components used in a splice in accordance with the present invention, namely, overlapping foil strips, and FIG. 16 is a top perspective of the strips of FIG. 15 assembled and conformed to a cooperating component;

FIG. 17 is a somewhat diagrammatic top perspective of the strips of FIG. 15 and FIG. 16 assembled with other components of the splice of the present invention;

FIGS. 18, 19 and 20 are corresponding, diagrammatic, longitudinal vertical sections illustrating different stages of cord repair using the foil strips of FIGS. 15–17;

FIG. 21 (on the drawing sheet with FIGS. 15–17) is a top perspective of a modified foil strip usable in the present invention;

FIG. 22 is a top perspective of an alternative splice in accordance with the present invention, and FIG. 23 is a corresponding top perspective of the splice of FIG. 22 with parts in different positions;

FIG. 24 is a top perspective of another embodiment of a splice in accordance with the present invention;

FIG. 29 is a top perspective of another embodiment of a splice in accordance with the present invention, FIG. 30 is a somewhat diagrammatic end elevation of the splice of FIG. 29, and FIG. 31 is a longitudinal vertical section of the splice of FIG. 29;

FIG. 32 is a top perspective of an alternative splice in accordance with the present invention, and FIG. 33 is a top perspective of the splice of FIG. 32 with parts in different position;

FIG. 35 is a top perspective of another embodiment of a splice in accordance with the present invention, with parts shown in exploded relationship, FIG. 36 is a top perspective corresponding to FIG. 35 but with parts assembled, FIG. 37 is a longitudinal vertical section of the splice of FIG. 35, and FIG. 38 is a fragmentary transverse vertical section of the splice of FIG. 35;

FIG. 39 is a fragmentary top perspective of an end portion of a splice of the general type shown in FIG. 35 but with a modified external component, and FIG. 40 is a fragmentary transverse vertical section illustrating the modified external component of FIG. 39;

FIG. 41 is a fragmentary transverse vertical section of a splice of the general type shown in FIG. 35, but with a first modified internal component, FIG. 42 is a fragmentary transverse vertical section corresponding to FIG. 41 but with a second modified internal component, FIG. 43 is a fragmentary transverse vertical section corresponding to FIG. 41 but with a third modified internal component, FIG. 44 is a fragmentary transverse vertical section corresponding to FIG. 41 but with a fourth modified internal component, and FIG. 45 is a horizontal section along line 45–5 of FIG. 41;

FIG. 46 is a top perspective of another embodiment of a splice in accordance with the present invention with parts shown in exploded relationship, and FIG. 47 is a top perspective corresponding to FIG. 46 but with parts assembled;

FIG. 48 is a top perspective of another form of a splice in accordance with the present invention with parts partially assembled;

FIGS. 49 and 50 are corresponding top perspectives of a repair system in accordance with the present invention, illustrating an alternative way of securing a splice to a damaged connective cord;

FIG. 51 is a top perspective of another embodiment of a splice in accordance with the present invention, with some parts shown in exploded relationship, and FIG. 52 is a fragmentary enlarged top plan of a portion of the splice of FIG. 51;

FIG. 53 is a top perspective of another embodiment of a splice in accordance with the present invention, and FIG. 54 is a fragmentary side elevation of a portion thereof;

DETAILED DESCRIPTION OF THE PREFERRED EMBODIMENT

Figure 1:
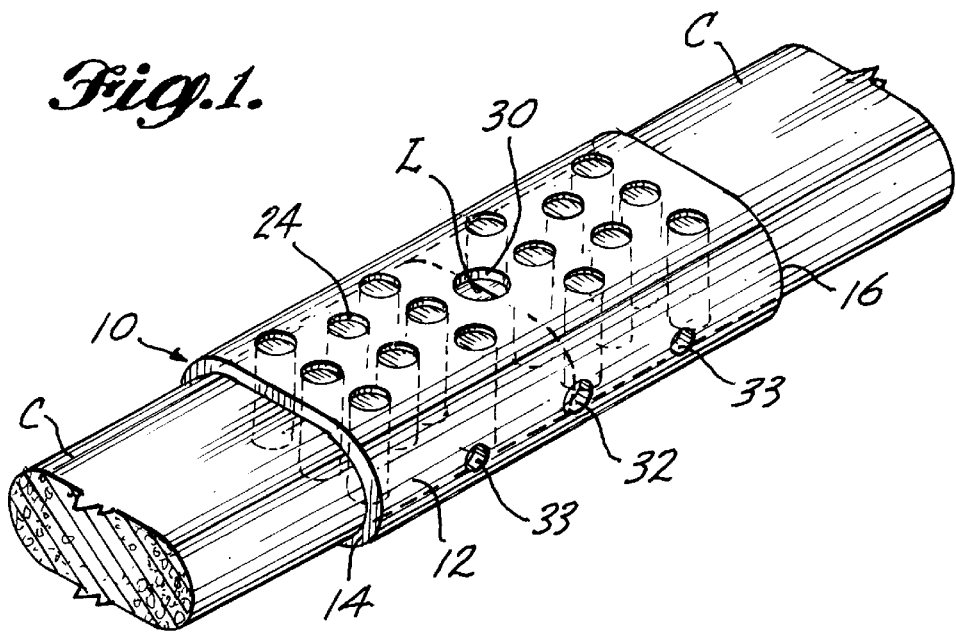
FIG. 1 is a top perspective of a severed fibrous cord of connective tissue repaired in accordance with the system of the present invention.
Figure 2:
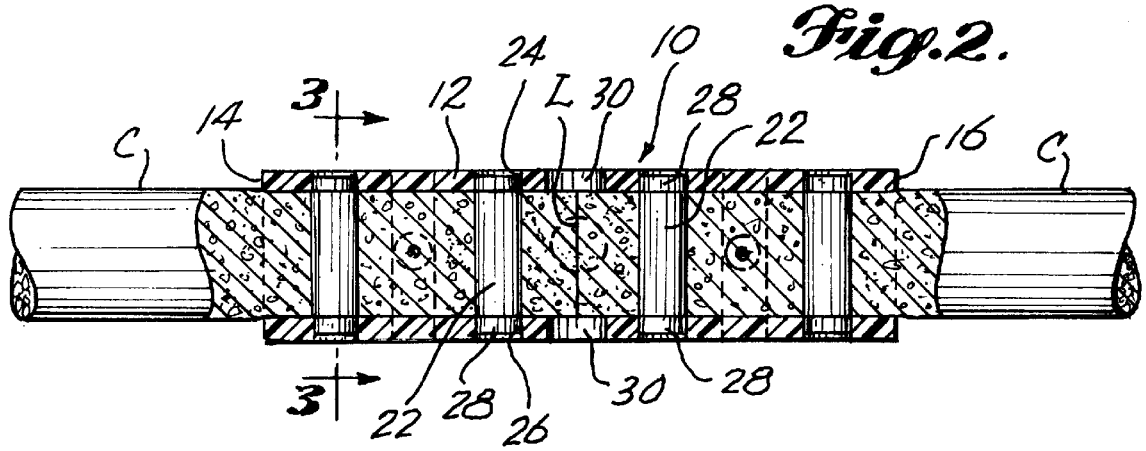
FIG. 2 is a side elevation of the repaired cord of FIG. 1, with parts broken away.
Figure 3:
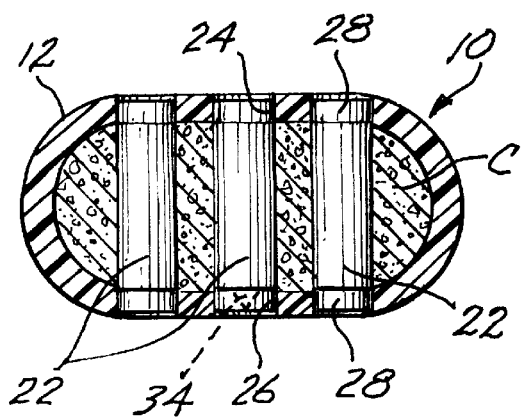
FIG. 3 is a vertical transverse section along line 3—3 of FIG. 2.

The splice of the present invention is used for repairing lacerated or severed fibrous connective tissue ("connective cords"), particularly ligaments and tendons. One embodiment of the splice 10 is illustrated in FIGS. 1, 2 and 3 in conjunction with a connective cord C, such as a flexor tendon, separated at a location L intermediate its opposite end connections (not shown) to adjacent bone and muscle. Relative sizes of the cord and splice components are exaggerated in the drawings for ease of illustration and description.

The primary component of the splice 10 is a unitary, substantially rigid or semi-rigid sleeve 12. The interior of the sleeve is of substantially uniform cross section from one end 14 to the other end 16, sized to snugly receive the severed end portions of the cord. The separation location L is situated midway between the sleeve ends. In accordance with the present invention, the cord end portions are secured within the sleeve so as to maintain the separated ends in abutting relationship to promote healing. In addition, the severed end portions are interconnected with the sleeve for substantially uniform distribution of force across the cord. Tension can be applied to the cord through the splice even before any healing has occurred, thereby enabling normal functioning of the repaired cord immediately or soon after the repair. Thus, in characterizing the sleeve as preferably being "rigid or semi-rigid", one important characteristic is that the dimensions and general shape of the sleeve not change substantially as normal tension is applied to a cord secured in the sleeve, it being particularly important that force applied to the cord be transmitted through the sleeve. In the case of a severed cord, it is desirable for the severed ends of the cord to abut within the sleeve and maintain the abutting relationship despite tension being applied to the cord. Further, as described in more detail below, in the case of mechanical fasteners for securing a cord within the sleeve, preferably the rigid or semi-rigid character of the sleeve results in the fasteners being stably positioned without substantial deflection caused by tension applied to the cord.

For many connective cords, including flexor tendons, severed cord ends maintained in abutting relationship will heal over time and gradually regain the pre-injury strength. In accordance with the present invention, the splice 10 can be formed of a rigid or semi-rigid bioabsorbable polymer. The ideal relationship of the strength of the splice as compared to the strength of the healing cord is illustrated in FIG. 4. As represented by line 18, initially (time "0") the abutting severed cord ends will not inherently withstand tension whereas, as represented by line 20, at t-0 the splice and cord connection will withstand the entire maximum force to which the cord would be subjected in normal use. The splice weakens as it is absorbed into the body, as indicated by the downward slope of line 20. At the same time, the repair site heals and strengthens. Ideally, at each stage of healing the combined strength of the splice and the healing cord is at least equal to the maximum force to which the cord is normally subjected. In the case of a flexor tendon, normal healing is completed by about twelve weeks, at which time the tendon itself will withstand normal forces and the splice is no longer required. An appropriate blend of bioabsorbing polymer, such as polydioxanone (PDO), polyglycolic acid (PGA), polylactic acid (PLA) or a PGA/PLA copolymer, can be selected based on the healing characteristics of the particular connective cord repaired and the dimensional requirements for the splice in order to achieve the desired strength and bioabsorbing properties. In addition, the sleeve and/or the components securing it to the cord can be coated or impregnated with an agent or agents to enhance healing or decrease adhesion or scar formation such as hyaluronic acid, angiogenic factors, growth factors and/or collagenase inhibitors. Such agents can immediately diffuse into the body directly adjacent to the repair, and/or be released over time as the sleeve is absorbed.

In the case of connective cords that move along or through adjacent tissue, bone, etc., and particularly in the case of flexor tendons which pass through a series of fibro-osseous tunnels and pulleys of the hand, the cross-sectional shape of the sleeve 12 should approximate the shape of the connective cord when moving under tension. In the case of a flexor tendon, the cord is oval when under tension and, accordingly, the shell 12 is of oval cross section. In a representative application repairing a flexor tendon, the shell can have an inside upright minor axis dimension of about 0.094 inch and an inside horizontal major axis dimension at least about twice the length of the minor axis. The length of the splice shell must be large enough to allow securing of a sufficient segment of each severed end portion without application of localized forces that could further tear, lacerate or otherwise injure the cord ends. The sleeve also can be short enough to allow for bending of the flexor tendon through the pulley system of the hand. In a representative embodiment as used for repairing a flexor tendon, the length of the sleeve 12 can be about 0.340 inch, substantially greater than the maximum cross-sectional dimension. For smooth gliding, the shell wall should be as thin as possible, about 0.025 inch to 0.029 inch in a representative embodiment, and certainly much less than one-half the minor axis of the sleeve. The ends of the sleeve can be chamfered to ease sliding of the sleeve.

In the embodiment illustrated in FIGS. 1, 2 and 3, the severed end portions of the cord C are interconnected with the sleeve by pins 22 extending between the top and bottom walls of the sleeve. Several pins are provided at each side of the separation location L, preferably arranged in transversely extending rows. To prevent application of localized forces when the cord is under tension, pins of each row at each side of the separation location are staggered relative to the pins of an adjacent row. Also, it is preferred that the pins be of small diameter, approximately 0.023 inch to 0.032 inch in the representative embodiment, and at each side of the separation location the pins should be spaced apart a distance at least as great as the pin diameter. In the illustrated embodiment, the pins are provided in a 3-2-3 staggered configuration at each side.

Each pin 22 extends through aligned holes 24 and 26 in the top and bottom sleeve walls, respectively. As described below, the pins 22 can be driven through the aligned holes. Preferably, each pin has opposite end portions 28 of slightly reduced diameter as compared to the central portion of the pin extending through the tendon, such that narrow shoulders of the pins abut against the inner periphery of the shell to maintain the pins in position. The outer ends of the pins preferably are substantially flush with the outer periphery of the sleeve so that they will not snag or irritate adjacent tissue.

Figure 9:
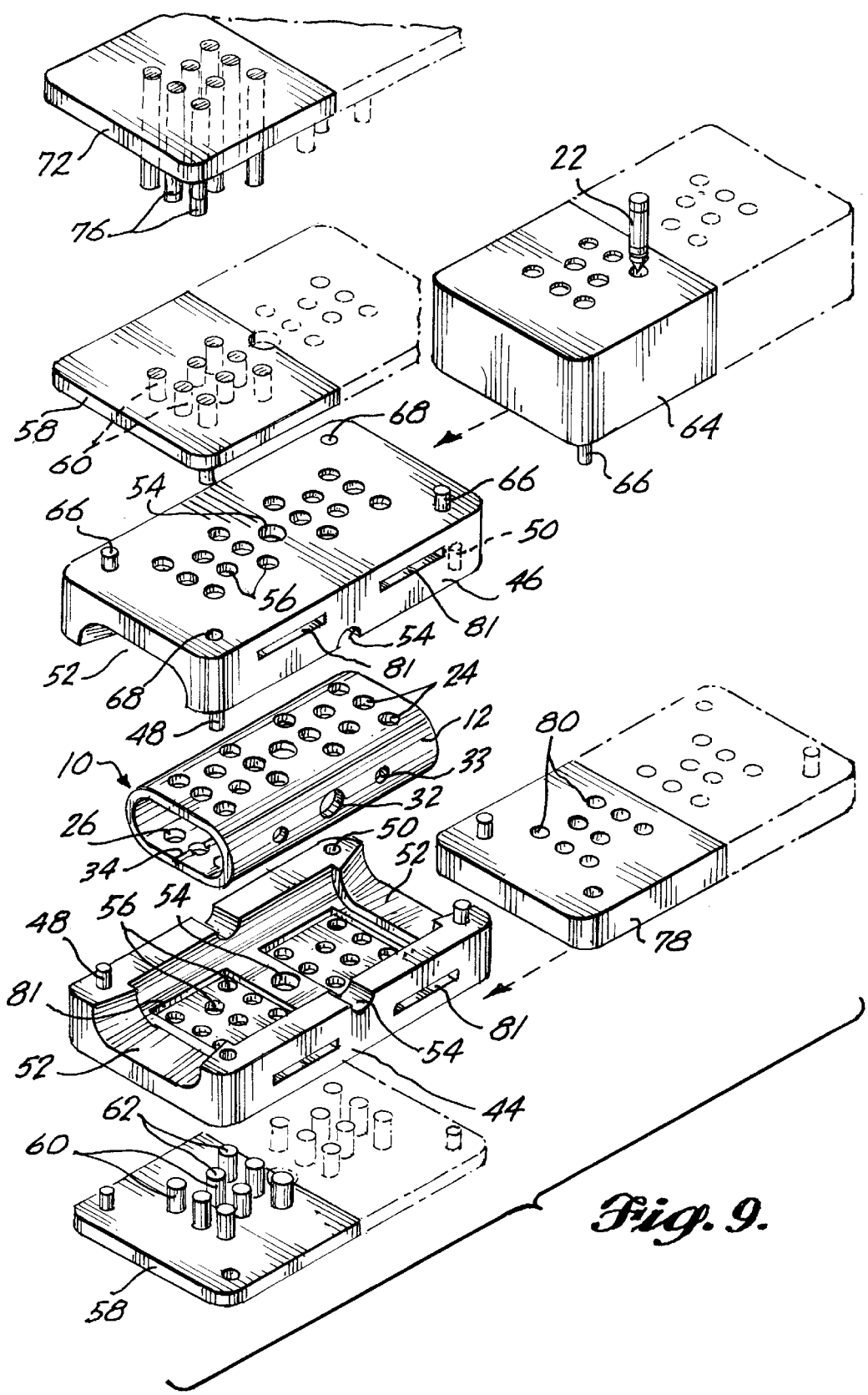
FIG. 9 is a top perspective of components of a splice in accordance with the present invention, with parts shown in exploded relationship.

The top and bottom walls of the sleeve have aligned observation ports 30 large enough that the cord ends may be viewed so that the separation location L can be precisely positioned at the center of the sleeve. In the representative embodiment, the observation ports can be about 0.050 inch in diameter. At the sides, additional central observation ports 32 are provided, as well as smaller ports 33 toward the ends for the purpose of permitting synovial fluid to diffuse into and through the shell to promote healing. Similarly, as seen in FIG. 9, the inner periphery of the shell can be provided with one or more V grooves 34 to allow blood flow to the cord. The sizes of ports 33 and groove 34 are not critical, except that care must be taken that the additional ports and groove(s) do not unduly weaken the sleeve.

With reference to FIG. 5 and FIG. 6, each pin 22 can be molded of a suitable polymer with the reduced diameter end portions 28 forming the narrow, outward facing annular shoulders 36 for engaging against the inner periphery of the sleeve adjacent to the holes through the top and bottom sleeve walls. For ease of insertion of the pins through the tendon, each pin can be formed with a sharpened tip portion 38 projecting from one pin end portion 28. A peripheral groove 40 can be formed between the sharpened tip portion 38 and the adjacent end portion 28 for ease in cutting away the tip portion after insertion of the pin so that the remaining pin end will be flush with the outer periphery of the sleeve. Alternatively, the pin can be weakened sufficiently by the peripheral groove 40 that the tip portion can be broken off following insertion.

The modified pin 22' shown in FIG. 7 and FIG. 8 is substantially identical to the pin 22 shown in FIGS. 5 and 6, except that pin 22' is provided with a separate stainless steel sharpened tip 38' having a rear blind bore 42 for fitting on a corresponding cylindrical stud 43 molded integrally with the remainder of pin 22'. The stainless steel tip can be press fitted to or otherwise secured to the stud 43, such as by a suitable adhesive. In other respects, the pin of FIGS. 7 and 8 is identical to the pin previously described, including the peripheral groove 40 between the tip and the adjacent end portion 28.

FIG. 9 illustrates several repair components that can be used in securing a splice 10 in accordance with the present invention on an injured connective cord. Sleeve 12 can be embedded in a ferrule consisting of a bottom half 44 and a top half 46. The two ferrule halves can be brought together so as to enclose the peripheral wall of the sleeve. The ferrule halves can have mating registration pegs 48 and sockets 50 at the corners and meet at a central horizontal plane. When brought together, the ferrule halves define an interior cavity of approximately the same shape as the outer periphery of the sleeve 12, with flared entrances 52 at the opposite ends leading into the interior of the sleeve. The composite ferrule has observation ports 54 registered with the observation ports of the sleeve, and through holes 56 registered with the sleeve pin holes 24 and 26.

With reference to FIG. 10, the flared entrances 52 of the ferrule help to guide the severed end portion of a connective cord C into the splice sleeve 12. Additionally, the cord end portions can be compressed prior to insertion, preferably by a clamping tool which will apply a substantially uniform compressive force throughout the circumference of the cord end. Different methods may be employed for inserting the severed cord ends into the sleeve. A single suture can be used for pulling the first severed end into the sleeve, either by passing the suture material through the opposite end of the sleeve or through one of the sleeve ports. A second suture could be passed through one observation port, back to the second tendon end portion and through the opposite observation port for drawing the second end into the sleeve. As described briefly above, one or the other or both of the severed tendon end portions can be compressed prior to insertion. The compressed ends tend to maintain smaller diameter when the compression force is withdrawn for a long enough period of time that they can be inserted more easily into the sleeve.

Nevertheless, the cord end may have a tendency to catch on the exposed pin holes 24 or 26 of the sleeve. This problem can be alleviated by use of detachable plates 58 having cylindrical plugs 60 for filling the pin holes. The plugs are of a length so as to extend through the ferrule holes 56 and the aligned sleeve holes 24 or 26, with the inner ends 62 of the plugs lying flush with the inner periphery of the shell when the plugs have been fully inserted.

Preferably, one severed end portion of the cord is positioned in the splice shell and secured in position prior to insertion of the other severed end portion. FIG. 10 illustrates the positions of the parts with one severed end portion of the cord C (the end portion at the left) inserted into the ferrule-sleeve assembly. Thereafter, the plates 58 and plugs 60 are removed. Next, a cartridge 64 containing all eight pins for that side can be fitted on the top ferrule half 46, as shown in FIG. 11. The top ferrule half and pin cartridge can have mating pegs and sockets 66 and 68 to temporarily retain the cartridge in position with the captured pins 22 or 22' in alignment with the ferrule and sleeve pin holes.

Figure 12:
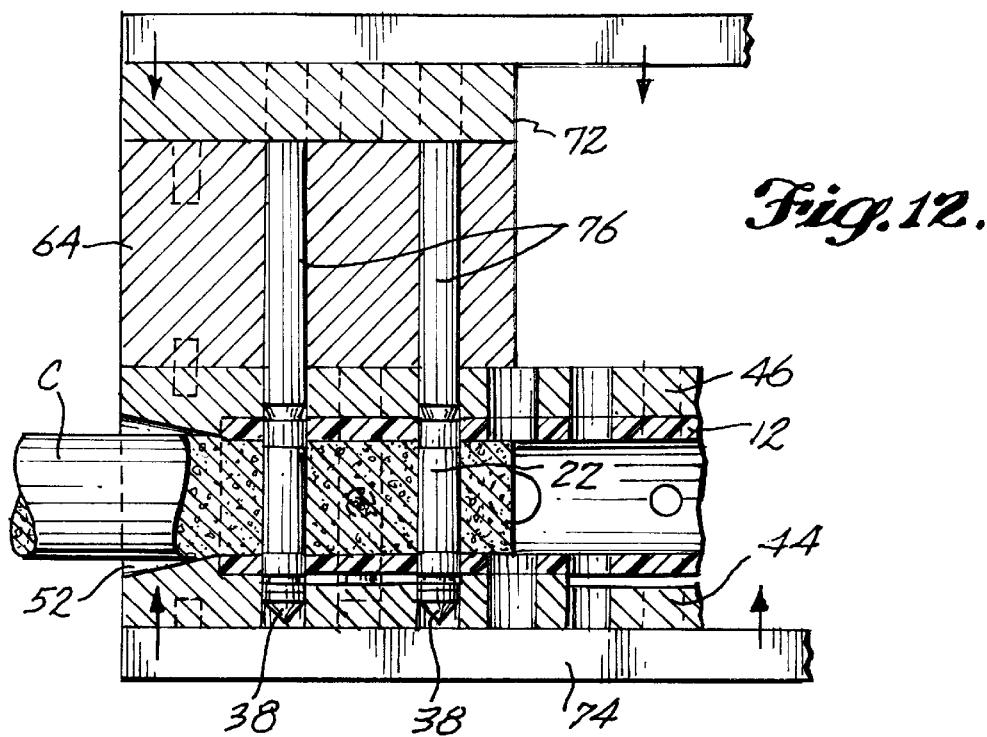

With reference to FIG. 12, all of the pins retained in the cartridge can be driven through the tendon simultaneously. This can be achieved by a tool having top and bottom jaws 72 and 74. The bottom jaw 74 forms a platen beneath the bottom ferrule half 44. Alternatively, the bottom jaw of the tool can engage a ledge or projection of the bottom ferrule half to hold it stably in position. The upper jaw 72 has downward projecting pusher rods 76 in alignment with the cartridge bores in which the pins 22 or 22' reside. Bringing the two jaws together has the effect of simultaneously thrusting the pins downward to the position indicated in FIG. 12 in which the upper ends of the pins are substantially flush with the upper periphery of the splice sleeve, and the sharpened ends 38 of the pins project downward below the bottom periphery of the sleeve.

Figure 13:
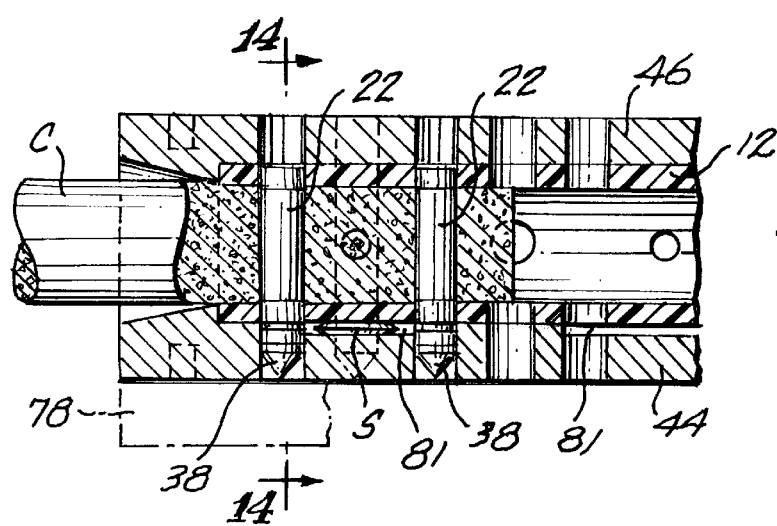
Figure 14:
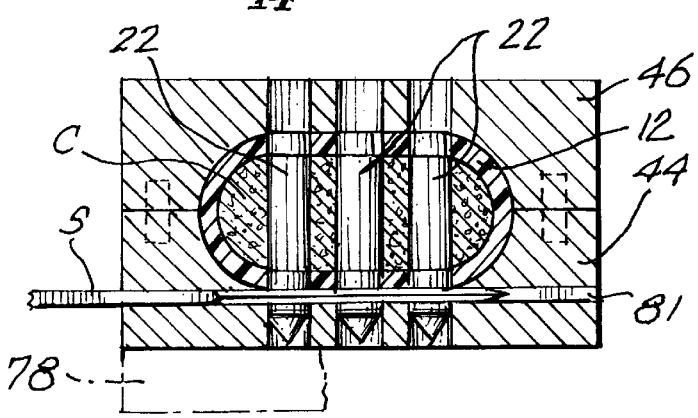
FIG. 14 is a transverse vertical section along line 14—14 of FIG. 13.

FIGS. 13 and 14 show the relative positions of the parts after the clamping tool and pin cartridge have been removed. The bottom ferrule half 44 preferably has a transverse slot 81 that passes immediately beneath the bottom periphery of the splice sleeve 12. A scalpel S or other cutting blade can be thrust through the slot 81 to sever the sharpened ends 38 or 38' from the bodies of the pins 22 or 22'. Thereafter, the process is repeated for the other severed end portion of the cord being repaired, whereupon the ferrule halves can be separated and removed and the repair is complete.

Preferably, the sharpened end portions 38 or 38' of the pins are sufficiently short that they will not protrude beyond the bottom ferrule half. However, if longer sharpened ends are used, a catch plate 78 can be attached below the bottom ferrule half, after the plugs are removed, with receptacles 80 (see FIG. 9) for receiving the projecting parts of the sharpened ends of the pins.

With reference to FIGS. 15 through 17, instead of plugging the holes of the sleeve to facilitate insertion of the cord ends, the interior of the ferruled sleeve can be lined with thin sheets 82 and 84 of a strong foil. Again, for ease of illustration and description, the dimensions are exaggerated, particularly the thicknesses of the foil sheets. The foil sheets include outer sheets 82 fitted inside the splice sleeve and inner sheets 84 fitted substantially contiguously against the outer sheets. Each outer sheet has a central aperture 86 that registers with the observation ports of the sleeve at the top and bottom. The outer sheets 82 also have larger generally rectangular cutouts 88 which expose the pin holes at one end of the sleeve. The inner sheets 84 have central apertures 90 which also align with the sleeve observation ports. Otherwise, the inner foil sheets 84 are generally rectangular and slightly narrower than the outer sheets 82, but of a width sufficient to cover the rectangular cutouts 88 of the outer foil sheets.

As seen in FIGS. 16 and 17, the outer sheets 82 are bent to conform to the shape of the passage running through the splice sleeve 12 and the ferrule 44, 46 in which the sleeve is received. The inner sheets 84 lie flat in the horizontal bottom and top of the sleeve and ferrule. Both the inner and outer sheets have narrow end tabs 92 that are secured to the upright end faces of the associated ferrule half, such as by a suitable adhesive or a spot-welding operation. When the foil sheets are fully assembled with the ferrule-sleeve unit (FIG. 17), the inner ends of all pin holes and ports are covered, with the exception of the observation ports at the top and bottom.

With reference to FIG. 18, a first severed cord end portion C can be slid inward through one of the flared entrances 52. Proper positioning can be achieved by viewing through the observation portals. If desired, the severed end portion of the tendon can first be compressed for easier insertion. With reference to FIG. 19, when the first severed end portion is positioned as desired, the inner foil strips 84 are removed from the ferrule-sleeve unit, in the same direction that the severed end portion of the tendon was inserted. The foil sheets can be detached or torn away from the opposite end of the ferrule. The pin holes aligned with the captured cord end portion then are exposed through the rectangular cutouts of the outer foil sheets 82, and the pins 22 or 22' at that end can be driven through the first severed end portion of the cord to secure it in position. Thereafter, as seen in FIG. 20, the second tendon end portion can be inserted from the opposite direction, followed by removal of the outer foil sheets 82. The outer sheets are slid out of the ferrule-sleeve unit in the same direction as the inner sheets, opposite the direction of insertion of the second cord end portion. The second cord end portion then can be secured by insertion of the pins 22 or 22' at that end of the ferrule-sleeve unit. Finally, the sharpened tips 38 or 38' of the pins are cut or broken off, and the ferrule halves are separated and removed.

In the modification shown in FIG. 21 (on the drawing sheet with FIGS. 15–17), a single foil strip 94 is used at the top and bottom of the sleeve, rather than overlapping strips. Each strip 94 has a central observation port 96 to align with the corresponding ports of the sleeve and ferrule. Narrow, transversely extending slots 98 extend inward from the opposite side edges of each strip 94, leaving small joining sections 99. The splice sleeve is lined with two such strips to obscure the pin holes. When one cord end has been inserted into the sleeve, the strip parts at that end are pulled to separate the strips at their centers by breaking the joining sections 99, and to expose the pin holes at that end. The other end portions of the strips remain in position obscuring the pin holes at the other end of the sleeve. The first cord end is secured to the sleeve as described above, whereupon the second cord end is inserted from the opposite end of the sleeve between the remaining parts of the foil strips. Such parts are then removed, and the second cord end is secured to the sleeve.

Testing was conducted with a prototype splice sleeve having the approximate dimensions given above, but with larger diameter pin holes and pins (approximately 0.033 inch) arranged in a 2-3 configuration at each side of the sleeve. Flexor tendons were harvested from fresh-frozen cadaveric hands. A tendon having a cross-sectional area approximately the same as the area encompassed by the inner periphery of the prototype sleeve was selected and severed using a surgical scalpel. The severed tendon end portions were fitted in the splice sleeve and secured with five pins at each side. The splice sleeve was formed of a polyimide polymer, nonbioabsorbable but similar in physical properties to bioabsorbable polydioxanone. One free end of the spliced tendon was clamped to a stationary block. The remaining free end was clamped to a low friction slide which, in turn, was secured to a cable. The cable was suspended over a single pulley and different weights then were secured to the hanging cable end to apply different tensile loads to the spliced tendon.

The spliced tendon remained in place at a tensile load of 46.9 Newtons (4.78 kilograms of vertical load) for 66 seconds at which time the testing structure, not the splice, failed. The splice, with the tendon and pins in place, was removed from the testing structure and examined. No evidence of failure was seen. The cut tendon ends remained visibly opposed within the observation portals, with no evidence of separation or gapping at the repair site. In contrast, similar testing was performed using flexor tendons "repaired" by suturing. The suture repair site showed signs of visible gapping upon application of 16.7 Newtons to 21.6 Newtons (1.70 to 2.20 kilograms of vertical load). The sutured repair failed immediately when tensile load was increased to 24.5 Newtons (2.50 kilograms of vertical load).

After repeat testing, some splitting of the tendon fibers adjacent to the connection pins was seen at higher forces. Consequently, it is preferred that the number of pins be increased and that the pin diameter be decreased to about 0.023 inch to 0.025 inch for a more uniform application of force throughout the repair site. The surprisingly strong forces that can be withstood without substantial separation of the abutting severed ends indicates that the splice can be used for connective cords stressed at higher loads than those normally applied to flexor tendons.

In the embodiment shown in FIGS. 22 and 23, the modified sleeve 100 has a long integral hinge joint 102 along one side. The sleeve can be opened in clamshell fashion to the position shown in FIG. 22 for reception of the severed end portions of the cord. Thereafter the sleeve can be closed to the condition shown in FIG. 23. The top and bottom portions of the sleeve have aligned holes 24 for pins 22, 22' of the type previously described. Preferably, a central observation port 30 is provided in at least the top of the sleeve. At the side opposite the hinge joint 102, the sleeve has flanges 104 that abut when the sleeve is closed. The flanges can be stapled, clipped, sutured or otherwise secured together to maintain the sleeve in the closed position. Sleeve 100 has the same physical characteristics as the previously described embodiment. More than one longitudinally extending hinge joint can be used at the closed side of the sleeve.

Depending on the application, it may be desirable for the sleeve in accordance with the present invention to flex or bend for smooth excursion of the repaired cord. In the embodiment illustrated in FIG. 24, the modified sleeve 110 has an array of openings 112 designed to enhance flexing or bending of the sleeve, without altering its rigidity in a longitudinal direction or its ability to rigidly anchor the connection pins. Stated in another way, although the sleeve can bend or flex, preferably it will not change its longitudinal dimension substantially which could alter the abutting relationship of the severed ends of the cord C, and preferably the transverse cross-sectional shape is not altered substantially. It is most important that the sleeve be able to bend or flex in the direction of its minor axis, i.e., up and down as viewed in FIG. 24. The pattern of openings 112 can be selected to allow greater flexibility of the sleeve in that direction while minimizing longitudinal deflection. As for the previously described embodiments, the cord ends can be secured in the sleeve by pins 22 extending through aligned holes 24 in the top and bottom surfaces of the sleeve.

Figure 26:
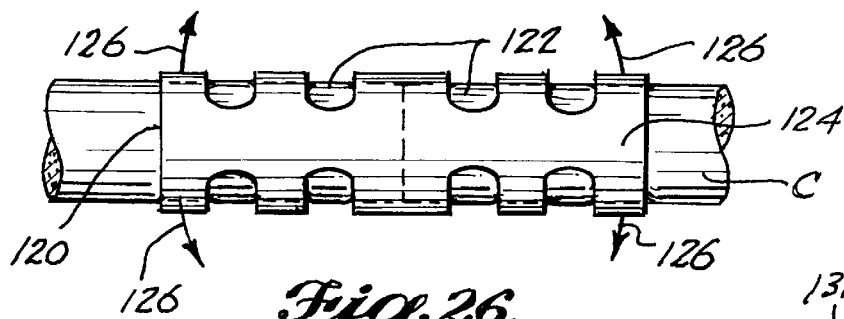
FIG. 26 is a side elevation of the splice of FIG. 25.
Figure 25:
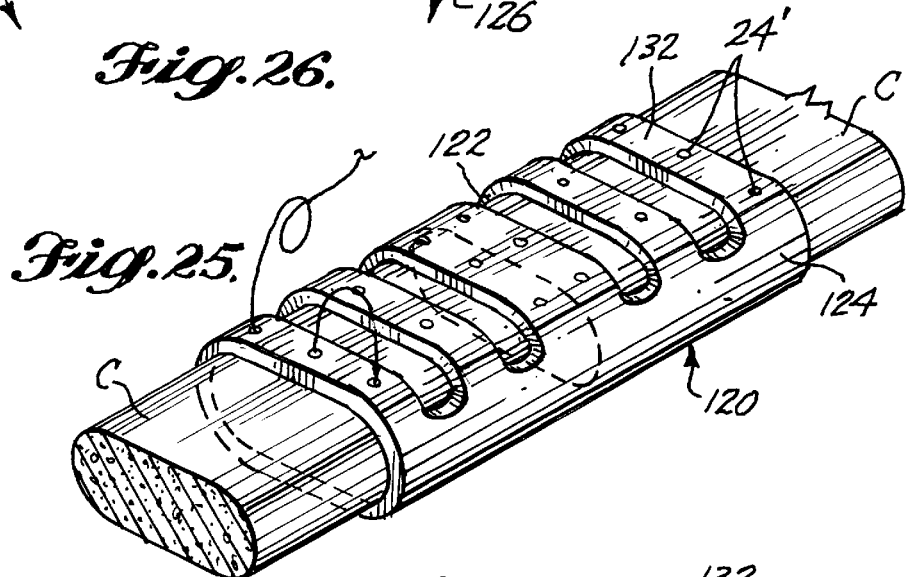
FIG. 25 is a top perspective of another embodiment of a splice in accordance with the present invention.

FIGS. 25 and 26 illustrate another embodiment of a sleeve in accordance with the present invention designed to flex in the direction of the minor axis. The unitary sleeve 120 is formed with transversely extending slots 122 at the top and bottom. There still remains a continuous longitudinally extending rib 124 at each side. Tension applied to the cord still is transmitted through the sleeve lengthwise, but increased bending or flexing of the sleeve in the direction indicated by the arrows 126 in FIG. 26 is permitted.

Sleeve 120 of FIGS. 25 and 26 can be connected to cord ends to be repaired by pins as for the previously described embodiments. An alternative is to suture the rigid or semi-rigid sleeve to the cord ends, such as through holes 24'. If suture is used, it is important that the sleeve be rigid enough that the suture can be tightened substantially. The tensioned sections of suture extending between opposite walls of the sleeve act substantially the same as rigid pins.

Figure 28:
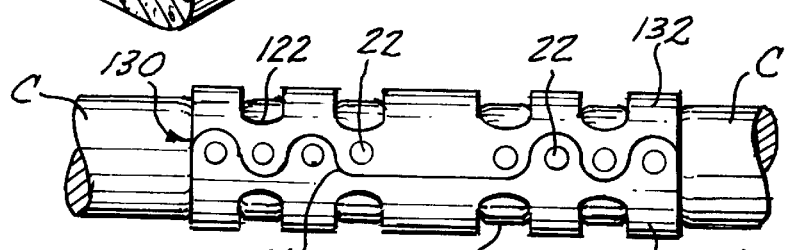
FIG. 28 is a side elevation of the splice of FIG. 27.
Figure 27:
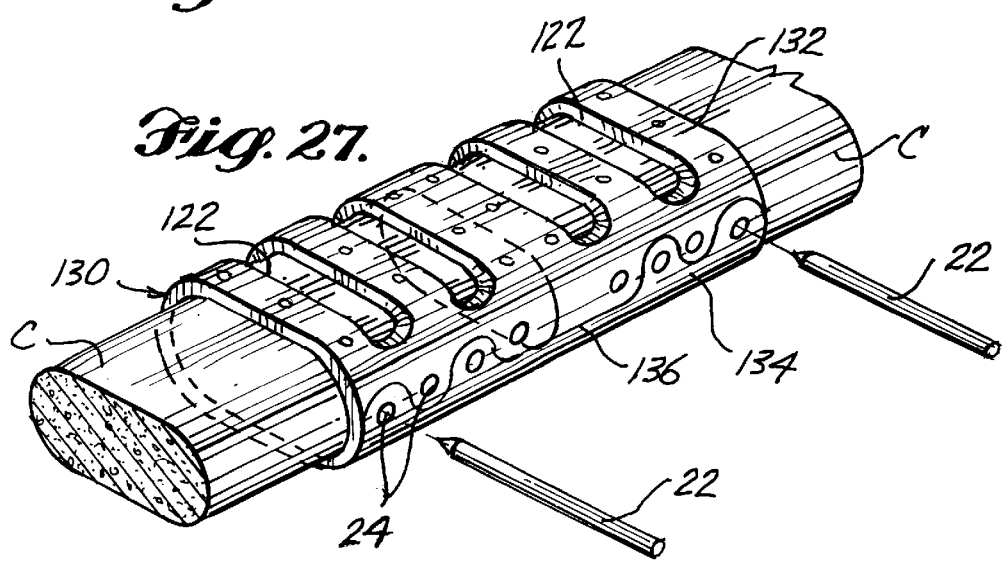
FIG. 27 is a top perspective of another alternative form of a splice in accordance with the present invention.

The embodiment illustrated in FIGS. 27 and 28 is similar to the embodiment shown in FIGS. 25 and 26 in that the sleeve 130 has transversely extending slots 122 in the top and bottom. However, sleeve 130 has separate top and bottom pieces 132 and 134, respectively. The top piece 132 and bottom piece 134 meet substantially contiguously at the sides along a scalloped border 136. The cord ends can be held within the sleeve by horizontal pins extending transversely between aligned holes 24 in the opposite sides of the sleeve, and/or by sutures.

FIGS. 29, 30 and 31 show another clamshell embodiment of the present invention where the top and bottom sections of the sleeve 140 are joined at one side by an integral hinge joint 142. Similar to previously described embodiments, the top section 144 and bottom section 146 each have transversely extending slots 122 to promote flexing of the sleeve in the direction of its minor axis. In addition, rather than having separate pins driven through the sleeve, the sleeve is formed with integral straight pins 148 extending upward from the bottom section 146, in alignment with the slots 122 of the top section. The top section 144 is formed with integral pins 150 which are curved approximately concentric with the axis of the hinge joint 142. Pins 150 preferably are aligned with the slots 122 in the bottom section of the sleeve. In use, the severed ends of the cord C are fitted in the bottom section of the sleeve, over the vertical pins 148. The top portion of the sleeve is closed, thereby puncturing the cord ends and further securing them by the curved pins 150. If pins 150 were straight, the collagen fibers would tend to be torn as the straight pins were rotated about axis 142. By curving the pins approximately concentric about the hinge joint, a less damaging puncture of the cord is obtained. Thereafter, the projecting end portions of the pins can be cut flush with the exterior of the sleeve. The sleeve can be held in the closed position by clips, staples, or sutures, for example.

Another clamshell embodiment of the present invention is shown in FIGS. 32 and 33. Sleeve 160 has a bottom section 162 with an array of rigid pins 164 projecting vertically upward therefrom. Two side-by-side top sections 166 are provided, joined to the bottom section 162 by integral hinge joints 168. The two top or "lid" sections 166 are spaced apart at the center of the sleeve. With the lids open, as illustrated in FIG. 32, the cord end portions and sleeve are moved relative to each other for piercing the cord end portions and retaining them in position, with the cord ends abutting at approximately the center of the sleeve. Thereafter, the lids 166 can be closed. The lids have lock tabs 170 that fit over projections 172 along the adjacent edge of the bottom section of the sleeve. Pins 164 project through holes 176 in the top sections. When the lid sections have been closed, the projecting end portions of the pins can be cut flush with the exterior of the sleeve. Preferably, the pins are provided in transversely extending rows, with the pins of each row staggered relative to the pins of the most closely adjacent row, and with each pin spaced from the adjacent pins by an amount equal to at least the diameter of a pin.

Figure 34:
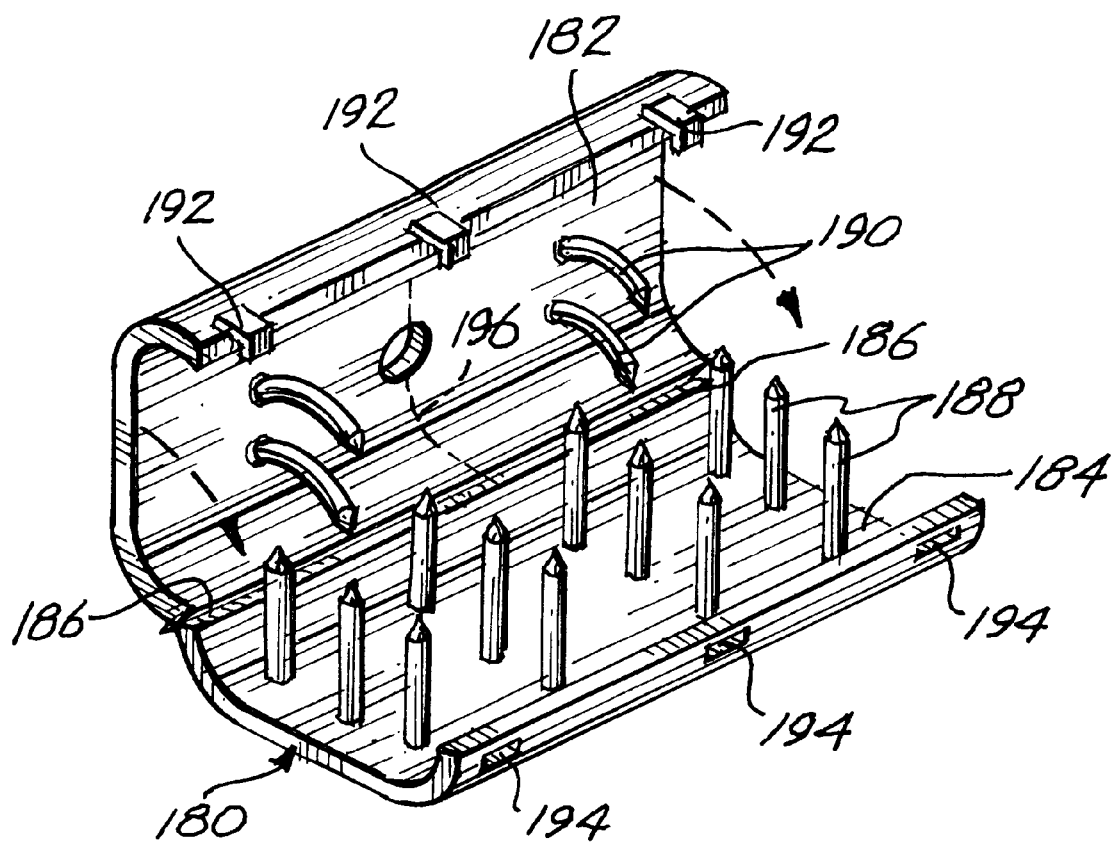
FIG. 34 is a top perspective of another embodiment of a splice in accordance with the present invention.

In the additional clamshell embodiment of the present invention shown in FIG. 34, sleeve 180 has a top section 182 joined to a bottom section 184 by an integral hinge joint 186 at one side. Straight integral pins 188 project upward from the bottom section 184, and pins 190, curved approximately concentric about the axis of the hinge joint, project downward from the top section 182. Pins 190 form a transverse row between rows of pins 188. All pins have sharpened tips, but are sufficiently short that they will not penetrate or extend into the opposing section when the splice is closed. Splice 180 can be maintained in the closed position by hooked lock tabs 192 at the free edge of the top section fitting into depressions or holes 194 along the free edge portion of the bottom section. With the splice closed, the pins are arranged in rows with a 3-2-3 staggered configuration at each side of the centerline. As represented by the broken line 196, the lid can be formed in separate pieces such that one severed end portion of a cord could be fixed in place and have the corresponding top section or lid closed, followed by securing the other severed cord end portion in position.

In the embodiment shown in FIGS. 35–38, the modified splice 200 in accordance with the present invention has separate top and bottom sections 202 and 204, respectively. The bottom section has straight rigid pins 206 projecting upward therefrom in alignment with transverse slots 208 through the top section. Similarly, the top section 202 has pins 210 projecting downward in alignment with transverse slots 212 of the bottom section. When the top and bottom sections are brought together, the free end portions of the pins fit in the slots of the other section, as best seen in FIG. 37. This helps to assure that the pins are held firmly in a vertical position without deflecting. The projecting sharpened tips of the pins can be cut flush with the periphery of the sleeve.

In addition, the bottom section has an undercut shoulder 214 extending lengthwise along its upper edge portions, to mate with a corresponding lip 216 of the top section. The lip 216 interfits with the undercut shoulder portion as best seen in FIG. 38 for holding the top and bottom sections together after the severed cord ends have been secured in position.

Alternatively, as seen in FIG. 39 and FIG. 40, the top and bottom sections 202 and 204 can be held together by a spring clip 217 having hooked end portions 218 for fitting in slots 220 of the top and bottom sections. Preferably, the body of the clip fits snugly in a shallow recess or groove 222 formed in each of the top and bottom sections such that the periphery of the clip lies flush with the periphery of the splice.

The internal pins 206 can extend through the slots in the other component, as described above, or, as seen in FIG. 41, shorter integral pins 206' can be used, such that they do not penetrate the opposing section. In that event, it still is preferred that the pins project substantially beyond the midline of the splice in order to transmit force more uniformly through the area of the cord held in the splice.

As seen in FIG. 42, another alternative is for the pins 226 from one section to be received in cylindrical sockets 228 formed integrally with the opposing section. Sockets 228 can be formed with sharpened tips. The cylindrical sockets 228 help to rigidify the pins 226 and prevent them from deflecting when load is applied to the cord.

With reference to FIG. 43, pins from one section can be formed as cylindrical bosses 230 having sharpened tips 232 designed to pass through small holes in the opposing section. The tip portion of each pin can have a neck 234 of reduced diameter which engages in the corresponding hole to achieve a snap fit connection. The periphery of the opposing section can have a depression 236 such that the sharpened tip 232 of the pin does not project beyond the outermost reaches of the periphery of the opposing section.

Another alternative is illustrated in FIG. 44 and FIG. 45. Pins 238 from one section are approximately semicircular in cross section. Pins 239 from the other section also are substantially semicircular in cross section and abut with pins 238 along a diametrical plane. Each pin braces the other against longitudinal deflection.

FIGS. 46 and 47 illustrate another two-part sleeve 240 in accordance with the present invention. Such a sleeve consists of identical unitary collars 242 each adapted for being secured to one end portion of a severed cord. Each collar can be secured to its respective severed end portion by suture, rigid pins, or any other effective manner for transmitting force from the cord through the collar. Each collar has a tongue 244 at one side, in line with a tunnel 246 through a boss 248 of the other collar. In use, the cord end portions are secured within their respective collars, and the two collars are brought together such that the tongues 244 are received in the tunnels 246. The tongues can have ratchet teeth 250 for engaging an integral pawl 252 of the tunnel, to hold the pieces together in the condition illustrated in FIG. 47. In such condition, the severed ends of the cord C abut, and tension applied to the cord is transmitted through the composite sleeve 240.

The embodiment illustrated in FIG. 48 is similar to the embodiment illustrated in FIGS. 46 and 47, in that separate collars 242' are secured to the severed cord end portions, such as by suturing or rigid pins extending through opposing faces. One collar 242' (the collar at the top in FIG. 48) has transversely spaced bosses 252 at the top and bottom. Flexible line or rail members 254 extend from bosses 252, and through aligned holes in the bosses 256 of the other collar. After the severed end portions of the cord are affixed in their respective collars, the collars are brought together and held in position by tying off the projecting free end portions of the rails or by otherwise fixing the rails in the bosses 256 through which they otherwise would slide. Preferably the bosses 252,256 would have a lower profile and be a smooth transition from the periphery of the associated collar.

FIGS. 49 and 50 illustrate an alternative way of securing severed end portions of a cord C to a splice 260 in accordance with the present invention. Such splice encircles the severed cord end portions and has the desired staggered array of holes 262 in its top and bottom. After insertion of the cord ends, holes are punched through the cord in alignment with the holes 262. With reference to FIG. 50, a mold 264 is fitted over the sleeve. A quantity of settable plastic 266 is injected into the mold for flowing through the holes punched in the cord ends. After the plastic material has set, the mold is removed, and the plastic material is trimmed flush with the periphery of the sleeve 260.

The embodiment of the present invention illustrated in FIGS. 51 and 52 uses a composite sleeve 270 having two separate end collars 272 and 274 spaced apart by a center collar 276. The adjacent ends of adjacent collars can have matching undulating edges 278 including, for example, central humps or nose portions 280 on collars 272 and 276 received in central depressions or valleys 282 of collars 276 and 274, respectively. The separate collars are connected together by links 284 which permit limited resilient flexing of the collars relative to each other, particularly in the direction of the minor axis of the composite sleeve. The inner periphery of the sleeve preferably is smooth with no internal projections which would hinder fitting of the collars on the severed end portions of a damaged connective cord.

Links 284 can be formed integrally with connection pins 286 that project perpendicularly downward therefrom. Holes 288 are provided in the tops and bottoms of adjacent collars, with recesses 290 at the top sized to receive the links. When the pins are inserted downward through a cord, the tops of the links lie flush with the remainder of the periphery of the composite sleeve 270. The bottom ends of the pins can be sharpened and include necks 292 of reduced diameter for snapping into the holes 288 in the bottom surfaces of the collars. Any projecting portions of the sharpened tips at the bottom can be cut off. At least the upper portion of the middle collar 276 can have observation ports 293 for viewing the abutting end portions of the damaged cord to assure that they abut prior to insertion of the pins.

With reference to FIG. 52, the links 284 bridge between adjacent collars, such as collars 274 and 276, and can be dimensioned to space the collars apart slightly, so as not to inhibit the flexing movement of one collar relative to another. In addition, the bridging portions of the links can have weakening grooves 294 which assist in permitting the flexing movement, preferably without introducing a tendency of the links to expand or contract lengthwise. For example, it still is preferred that the length of the composite sleeve 270 not increase or decrease substantially due to forces applied to the repaired cord. In addition, limited sideways flexing of the sleeve (in the direction of the major cross-sectional axis) can be permitted by tapering the depressions 290.

The embodiment illustrated in FIGS. 53 and 54, similar to the embodiment shown in FIGS. 50 and 51, uses a multi-part composite sleeve 300 including end collars 302 and 304 spaced apart by a middle collar 306. As for the embodiment of FIG. 51 and FIG. 52, the collars have identical cross sections and are aligned lengthwise of the centerline of the sleeve. Separate pins can be provided for extending through registered holes in the tops and bottoms for securing the collars to the damaged cord to be repaired. In the embodiment illustrated in FIGS. 53 and 54, three rigid pins 308 are provided for each of the two end collars 302 and 304, joined at the top by flush bridging portions 310. The middle section has two pairs of pins 312, each pair forming a transversely extending row with its pins staggered relative to the pins of the end collars. The pins of each pair can be connected by a flush bridging portion 314. The pairs of pins 312 are arranged at opposite sides of the center of the sleeve such that each pair penetrates a different severed end portion of the damaged cord.

To allow flexing of the sleeve in the direction of its minor axis, connecting links 316 are provided at each side. One end of each link is pivotally connected to an end collar, and the other end of each link 316 is pivoted to the center collar 306. As seen in FIG. 54, the links are received in tapered recesses 318 which allow limited swinging of the links relative to the collars to which they are connected. The pivotal connection can be achieved by inward projecting buttons of the links being snap fitted in corresponding holes of the collars.

Figure 55:
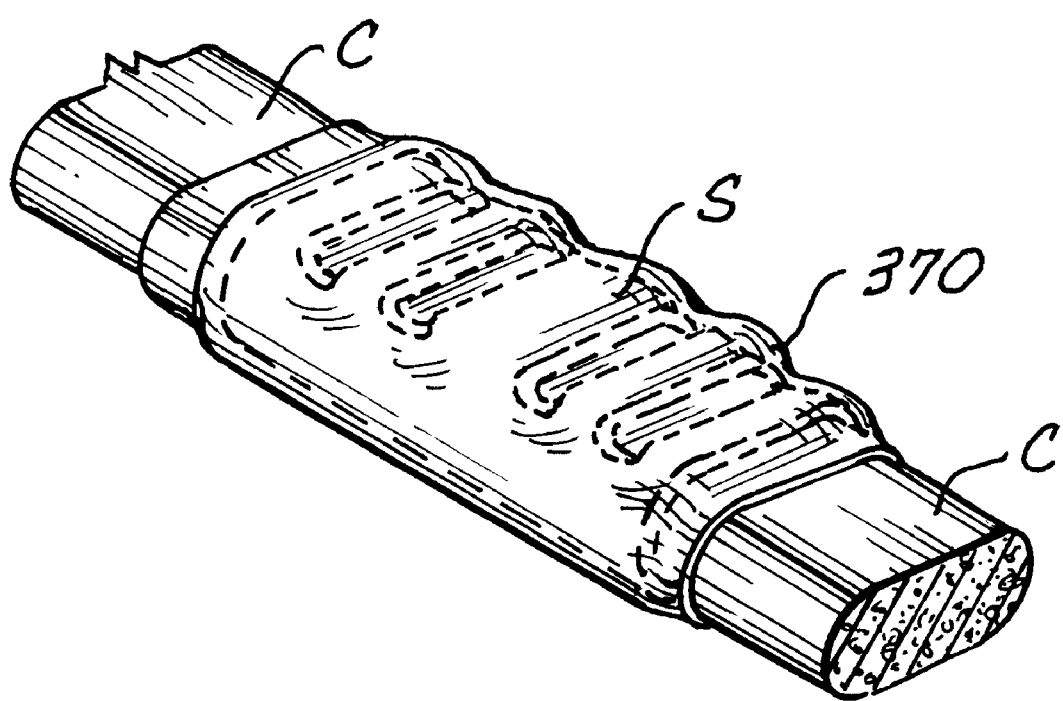
FIG. 55 is a top perspective of another component of the repair system in accordance with the present invention, namely, a coating for a splice or repair.

As noted above, in the case of a connective cord having substantial excursion relative to surrounding tissue, preferably the outer surface of a sleeve in accordance with the present invention (designated generically as "S" in FIG. 55) has a fairly smooth outer periphery. One method is to encapsulate sleeve S in a smooth outer covering 370. Such covering 370 can be a settable gel such as a hydrogel, a UV curing resin, a rigid or flexible outer shell or a sheet wrapped around the sleeve. Preferably, the coating covers at least a short marginal portion of each cord end C projecting from the sleeve S.

Figure 56:
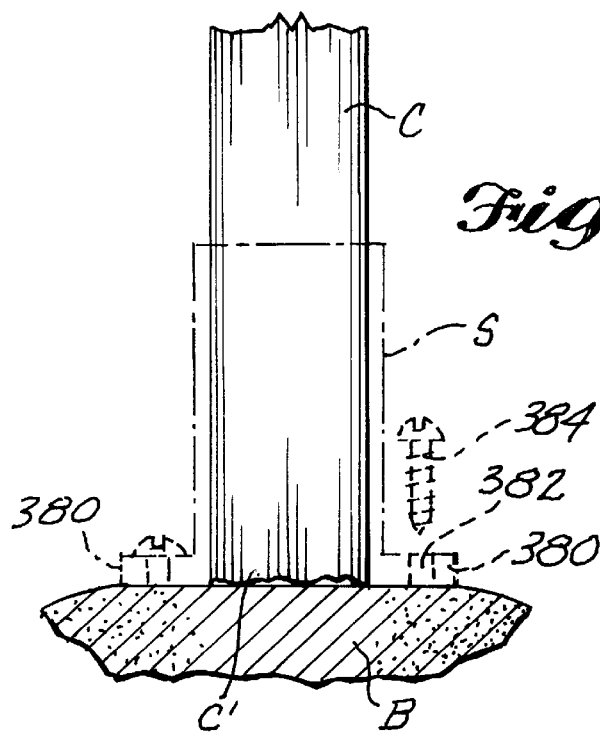
FIG. 56 is a diagrammatic perspective of a repair system in accordance with the present invention as used for connecting a damaged connective cord to a bone.

With reference to FIG. 56, sometimes a connective cord C, such as an ACL, will tear close to one of the bones B to which it should be stably connected. In that case, the damaged end portion of the cord can be secured in a sleeve of the type previously described (generically designated as "S" in FIG. 56), which sleeve is secured to bone B at the opposite end from which the cord extends. For example, the sleeve can be provided with mounting ears 380 having holes 382 for bone screws 384. If there is a short ligamentous stump C' remaining connected to the bone B, preferably such short stump is left attached to the bone to promote healing with the longer captured end of the cord. The cord can be secured within the sleeve by pins, tight sutures, or any other effective attachment mechanism, but preferably the sleeve still is rigid or semi-rigid such that tension applied to the cord is transferred through the sleeve to the bone.

Figure 57:
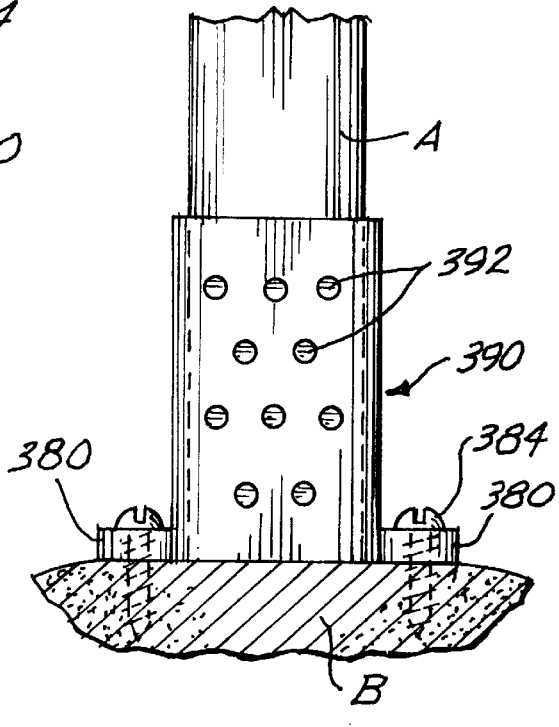
FIG. 57 is a perspective corresponding to FIG. 56 but illustrating a specific repair system in accordance with the present invention for connecting a damaged connective cord to a bone.

For example, in the embodiment illustrated in FIG. 57, the sleeve 390 is sized to receive an anterior cruciate ligament A and has four rows of holes 392 arranged in a staggered 3-2-3-2 configuration, such holes being provided in opposite sides of the sleeve. Pins of the type described above are inserted through the registered holes to secure the ligament in the sleeve. Tensional forces applied to the ligament are transferred through the sleeve, substantially uniformly throughout the cross section of the ligament, and to the bone by way of the connecting ears 380 and bone screws 384.

Figure 58:
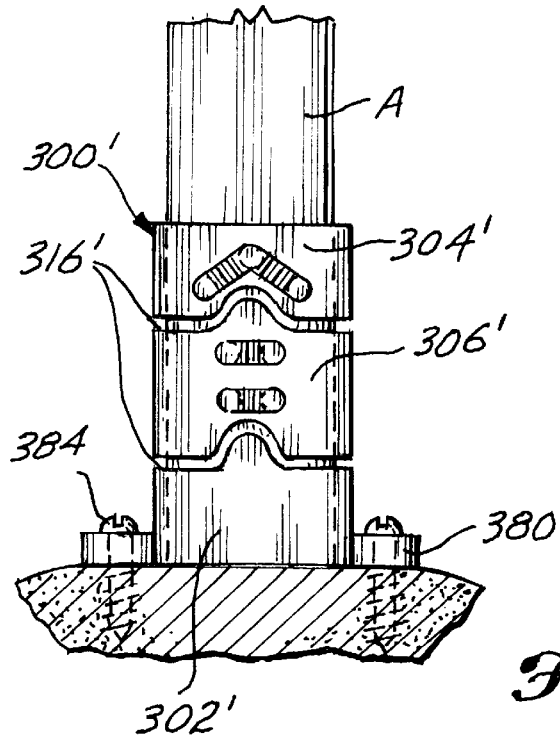
FIG. 58 is a perspective corresponding to FIGS. 56 and 57 illustrating an alternative repair system in accordance with the present invention as used for connecting a damaged connective cord to a bone.

Similarly, the embodiment illustrated in FIG. 58 uses a sleeve 300' of the type described with reference to FIGS. 53 and 54. However, one end collar 302' of the sleeve is provided with attachment ears 380 having holes for bone screws 384. The anterior cruciate ligament A has its severed end portion fitted through all three collars if little or no stump remains attached to the bone, to be secured therein by the pins arranged in the 3-2-2 configuration of collars 304' and 306'. Links 316' at the sides allow relative swinging movement of the separate collars 302', 306', 304' of the composite sleeve 300', without allowing any substantial relative longitudinal movement of the component parts of the sleeve. Consequently, tensional forces applied to the anterior cruciate ligament are transferred through the composite sleeve 300', with the forces preferably substantially uniformly distributed across the cross section of the ligament. Hinges 316' can be formed similar to the links 316 of the embodiment of FIGS. 53 and 54 so as to allow limited relative swinging movement of the collars in the direction of the major axis of the sleeve, in addition to limited swinging movement in the direction of the minor axis of the sleeve. If a substantial length of ligament remains attached to the bone, it can be fitted in collar 302'.

In each instance, it is desired that the damaged end portion of the cord be stably positioned relative to the bone and/or any remaining ligament material for a period of time sufficient to permit healing to occur.

Figure 59:
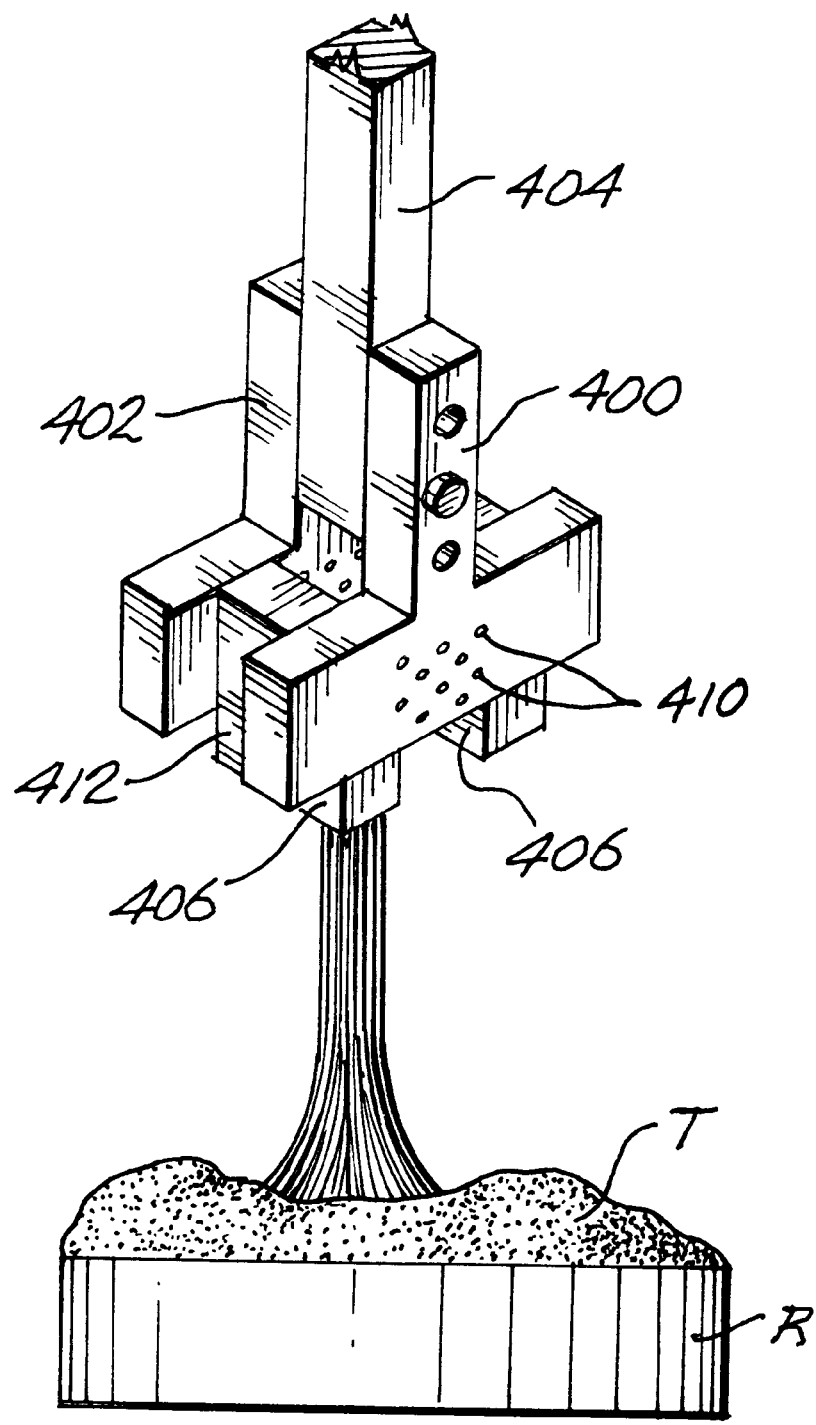
FIG. 59 is a top perspective of a test component used in evaluating a repair system in accordance with the present invention.

Additional testing was conducted to determine representative forces transmittable through a connection system in accordance with the present invention as used with an ACL. The ACL consists of multiple bundles. In one test, a single bundle was used, and in two additional tests, fall ligaments were used. For each test a ligament and its long attachments were harvested from a fresh frozen cadaver. The ligaments were severed close to the femur, but at the opposite end a tibial plug T was cut such that the tibial stump of the ligament remained attached to bone (see FIG. 59). The plug was secured in a ring R. The severed end portion of the ligament was inserted into a testing frame of the type shown in FIG. 59. Such frame has a top plate 400 and a bottom plate 402 connected together with an intervening spacer 404. Intermediate sideplates 406 were secured at the end of the testing frame opposite the spacer. A cord receiving recess was thereby formed at one end of the testing frame, of approximately square cross section, about 0.32"×0.32".

The top plate and bottom plate had aligned pin holes 410, each about 0.047" in diameter. The holes were provided in four transversely extending rows in a 2-3-2-3 configuration. Pins within each row were spaced about 0.08" apart, and the rows were spaced such that their centerlines were about 0.08" apart. In addition, the sideplates were provided with registered columns of holes 412, of the same diameter as holes 410 each column having four holes spaced 0.08" apart. The vertical columns were aligned, respectively, with the second and fourth horizontal rows, i.e., the horizontal rows containing three holes.

Figure 60:
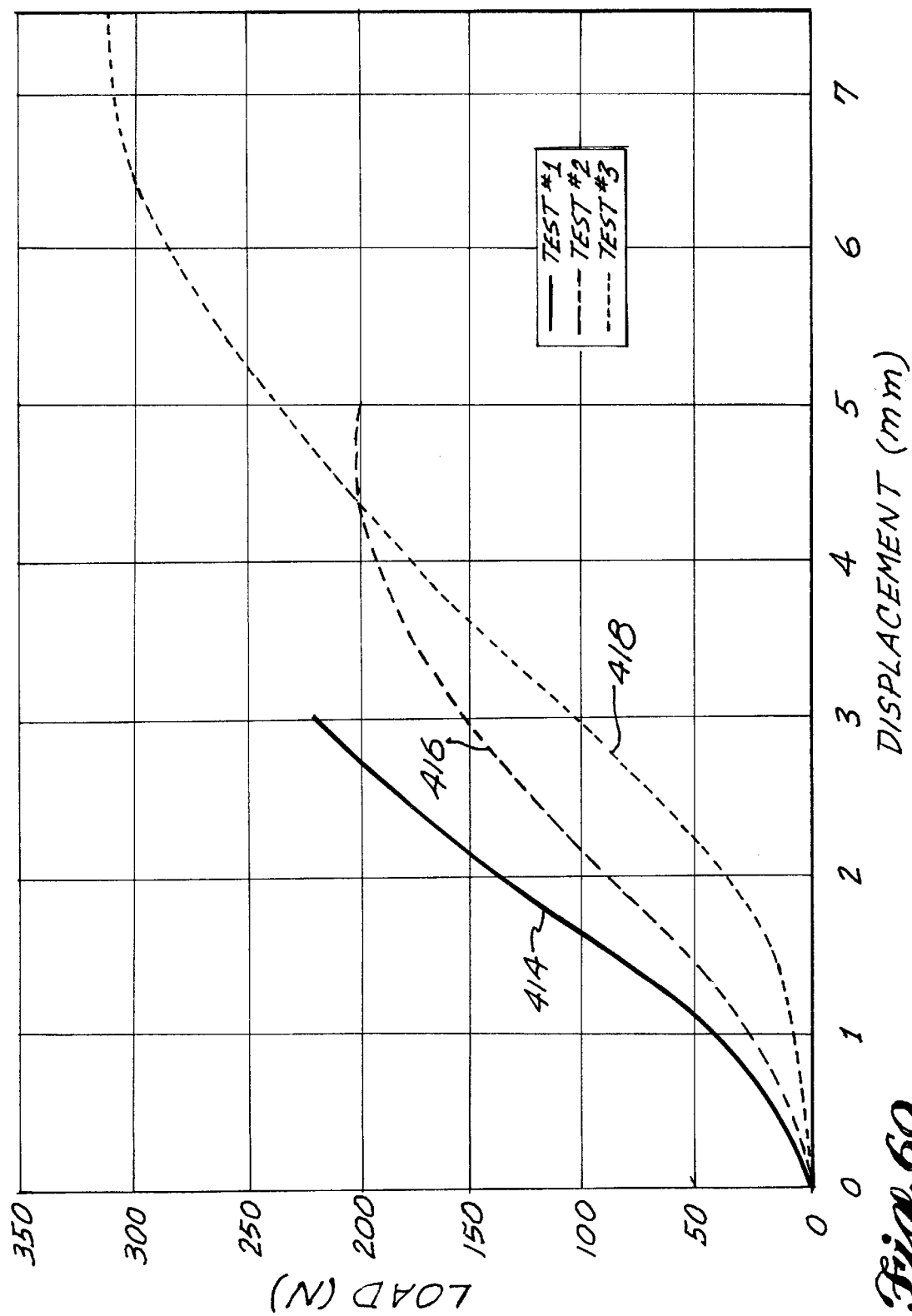
FIG. 60 is a graph representing results of testing a repair system in accordance with the present invention.

In a first test, the single ACL bundle, approximately 4 mm in diameter, was inserted into the opening of the test apparatus and pinned in place by vertical pins in the 2-3-2-3 configuration. Tension was applied by clamping the tibial plug, and force versus displacement measurements were taken, represented by line 414 of the graph of FIG. 60. There is some natural stretching of the cord, so that the fact of displacement does not indicate shifting of the cord in the test frame. Rather, except as noted below, the pinned end of the cord held fast in the frame.

In the first test, the cord tore from the testing apparatus under a force of 220 Newtons (49 pounds).

In a second test, a fall ACL was used, approximately 9 mm in diameter. This time the cord was pinned in the testing apparatus by two pins in each of the first and third rows, (the second and fourth rows having three rows each remaining empty) and by four pins in each of the two vertical columns. Line 416 shows the results. A load of 150 Newtons (33 pounds) was reached at 3 mm displacement. At 200 Newtons (44 pounds) the tibial plug fractured through cancellous bone with the ligament still held fast in the testing apparatus.

A third test using a full ACL approximately 9 mm in diameter was conducted, this time pinned using only the top and bottom holes with the pins in the 2-3-2-3 configuration. Line 418 shows the results. Three millimeters displacement was reached at 100 Newtons (22 pounds); and the ACL tore from the testing apparatus at a force of 310 Newtons (69 pounds).

In the ACL tests, the ligament was not circumferentially restrained as is desired in the present invention. Nevertheless, the substantial forces incurred prior to failure illustrate the usefulness of the system of the present invention for repair of an anterior cruciate ligament, including attachment to bone where appropriate.

Because of the different healing tendencies of the connective cords with which the present invention can be used, different materials or blends will be required for different applications. For example, an ACL heals quite differently from a flexor tendon, and will require materials that absorb over a much longer period of time to assure that adequate healing has occurred before the augmenting effect of the repair system in accordance with the present invention no longer is present.

While the preferred embodiments of the invention have been illustrated and described, it will be appreciated that various changes can be made therein without departing from the spirit and scope of invention. In addition, while the invention has been described with reference to humans, it also has application in animals.

What is claimed is:

1. A splice for a connective cord normally tensioned in the body during joint movement, said splice comprising a hollow sleeve of substantially rigid or semirigid material and sized for closely receiving a section of the cord, and means for securing the cord to the sleeve such that tension applied to the cord is transmitted through the sleeve, the sleeve being adapted for connection to a bone for connecting the connective cord to the bone and for transmission of tensional force from the connective cord through the sleeve to the bone, the sleeve including a first component adapted for connection to the bone and a second component adapted for securing to the cord, the first and second components being connected for relative swinging movement without substantially altering the length of the sleeve for maintaining the cord in substantially the same position relative to the bone during relative movement of the first and second components.

2. The splice defined in claim 1, in which the sleeve is adapted to receive a short ligamentous stump of the cord connected to the bone and maintain an adjacent portion of the cord in engagement with the stump.

3. The splice defined in claim 1, in which the sleeve is constructed for flexing in a direction transversely of its length without substantially altering the overall length of the sleeve.

4. The splice defined in claim 3, in which the sleeve is of generally oval cross section having a major axis longer than the minor axis, and in which the sleeve is constructed for flexing in the direction of the minor axis.

5. The splice defined in claim 1, in which the sleeve is open at both ends, having an unimpeded through bore.

6. The splice defined in claim 1, in which the securing means includes means for mechanically securing the cord to the sleeve such that tension applied to the cord is transmitted to the sleeve substantially uniformly throughout the cross section of the cord.

7. The splice defined claim 6, in which the securing means includes tensioned suture sections extending between opposing surfaces of the sleeve.

8. The splice defined in claim 6, in which the sleeve has opposite walls for extending along opposite sides of the cord, the securing means including several rigid pins extending between said walls.

9. The splice defined in claim 8, in which the pins are unthreaded.

10. The splice defined in claim 8, in which at least some of the pins are offset from each other.

11. The splice defined in claim 8, in which at least some of the pins project from one of the walls and are integral with said one wall.

12. The splice defined in claim 8, in which the pins have body portions extending between the opposite walls of the sleeve and opposite end portions received in the opposite walls of the sleeve, said pin end portions being of reduced diameter for forming shoulders for engaging against inner periphery of each of the opposite walls of the sleeve.

13. The sleeve defined in claim 8, in which the pins have opposite ends substantially flush with the outer periphery of the sleeve.

14. The splice defined in claim 8, in which the pins have body portions for extending through the interior of the sleeve, each pin having a sharpened end portion projecting from such body portion and a peripheral groove between the body portion and the sharpened end portion for separation of the sharpened end portion from the body portion.

15. The splice defined in claim 1, in which the sleeve is formed of separate sections, each of said sections being hollow and being substantially aligned axially with and adjacent section, and said sections being joined together.

16. The sleeve defined in claim 15, in which the sections are joined together for limited swinging movement relative to each other without a substantial change in the length of the sleeve.

17. The splice defined in claim 1, in which the sleeve is formed of bioabsorbable material.

18. The splice defined in claim 1, in which the sleeve is impregnated or coated with an agent selected from the group consisting of agents for enhancing healing, agents for decreasing adhesion formation, and agents for deterring scar formation.

19. The splice defined in claim 1, in which the sleeve is elongated and of substantially uniform cross section throughout its length.

20. The splice defined in claim 19, in which the length of the sleeve is substantially greater than the maximum cross sectional dimension of the sleeve.

21. The splice defined in claim 19, in which the sleeve has a peripheral wall of a thickness much less than the smallest cross-sectional dimension of the sleeve.

22. The splice defined in claim 1, in which the sleeve has opposite end portions, one end portion of the sleeve having projecting ears with apertures therethrough for receiving a connector to connect the sleeve to the bone.

23. The splice defined in claim 1, in which the sleeve completely encircles the connective cord.

24. The splice defined in claim 1, in which the sleeve has an inner periphery having a longitudinally extending groove to allow vascular flow to the cord.

25. A splice for a connective cord normally tensioned in the body during joint movement, said splice comprising a hollow sleeve of substantially rigid or semirigid material and sized for closely receiving a section of the cord, and means for securing the cord to the sleeve such that tension applied to the cord is transmitted through the sleeve, the sleeve being adapted for connection to a bone for connecting the connective cord to the bone and for transmission of tensional force from the connective cord through the sleeve to the bone, the sleeve having opposite walls for extending along opposite sides of the cord, the securing means including several rigid pins extending between said walls, the pins having body portions extending between the opposite walls of the sleeve and opposite end portions received in the opposite walls of the sleeve, said pin end portions being of reduced diameter for forming shoulders for engaging against the inner periphery of each of the opposite walls of the sleeve.

26. A splice for a connective cord normally tensioned in the body during joint movement, said splice comprising a hollow sleeve of substantially rigid or semirigid material and sized for closely receiving a section of the cord, and means for securing the cord to the sleeve such that tension applied to the cord is transmitted through the sleeve, the sleeve being adapted for connection to a bone for connecting the connective cord to the bone and for transmission of tensional force from the connective cord through the sleeve to the bone, the sleeve having opposite walls for extending along opposite sides of the cord, the securing means including several rigid pins extending between said walls, the pins having body portions for extending through the interior of the sleeve, each pin having a sharpened end portion projecting from such body portion and a peripheral groove between the body portion and the sharpened end portion for separation of the sharpened end portion from the body portion.

27. A splice for a connective cord normally tensioned in the body during joint movement, said splice comprising a hollow sleeve of substantially rigid or semirigid material and sized for closely receiving a section of the cord, and means for securing the cord to the sleeve such that tension applied to the cord is transmitted through the sleeve, the sleeve being adapted for connection to a bone for connecting the connective cord to the bone and for transmission of tensional force from the connective cord through the sleeve to the bone, the sleeve being formed of separate sections, each of the sections being hollow and being substantially aligned axially with an adjacent section, and the sections being joined together for limited swinging movement relative to each other without a substantial change in the length of the sleeve.

28. The splice defined in claim 27, in which the sleeve is adapted to receive a short ligamentous stump of the cord connected to the bone and maintain an adjacent portion of the cord in engagement with the stump.

29. The splice defined in claim 27, in which the sleeve is constructed for flexing in a direction transversely of its length without substantially altering the overall length of the sleeve.

30. The splice defined in claim 29, in which the sleeve is of generally oval cross section having a major axis longer than the minor axis, and in which the sleeve is constructed for flexing in the direction of the minor axis.

31. The splice defined in claim 27, in which the sleeve is open at both ends, having an unimpeded through bore.

32. The splice defined in claim 27, in which the securing means includes means for mechanically securing the cord to the sleeve such that tension applied to the cord is transmitted to the sleeve substantially uniformly throughout the cross section of the cord.

33. The splice defined in claim 32, in which the securing means includes tensioned suture sections extending between opposing surfaces of the sleeve.

34. The splice defined in claim 32, in which the sleeve has opposite walls for extending along opposite sides of the cord, the securing means including several rigid pins extending between said walls.

35. The splice defined in claim 27, in which the sleeve is formed of bioabsorbable material.

36. The splice defined in claim 27, in which the sleeve is impregnated or coated with an agent selected from the group consisting of agents for enhancing healing, agents for decreasing adhesion formation, and agents for deterring scar formation.

37. The splice defined in claim 27, in which the sleeve is elongated and of substantially uniform cross section throughout its length.

38. The splice defined in claim 37, in which the length of the sleeve is substantially greater than the maximum cross sectional dimension of the sleeve.

39. The splice defined in claim 27, in which the sleeve has opposite end portions, one end portion of the sleeve having projecting ears with apertures therethrough for receiving a connector to connect the sleeve to the bone.

40. The splice defined in claim 27, in which the sleeve completely encircles the connective cord.

41. A splice for a connective cord normally tensioned in the body during joint movement, said splice comprising a hollow sleeve of substantially rigid or semirigid material and sized for closely receiving a section of the cord, and means for securing the cord to the sleeve such that tension applied to the cord is transmitted through the sleeve, the sleeve being adapted for connection to a bone for connecting the connective cord to the bone and for transmission of tensional force from the connective cord through the sleeve to the bone, the sleeve having opposite end portions, one end portion of the sleeve having projecting ears with apertures therethrough for receiving a connector to connect the sleeve to the bone.

42. The splice defined in claim 41, in which the sleeve is adapted to receive a short ligamentous stump of the cord connected to the bone and maintain an adjacent portion of the cord in engagement with the stump.

43. The splice defined in claim 41, in which the sleeve is constructed for flexing in a direction transversely of its length without substantially altering the overall length of the sleeve.

44. The splice defined in claim 43, in which the sleeve is of generally oval cross section having a major axis longer than the minor axis, and in which the sleeve is constructed for flexing in the direction of the minor axis.

45. The splice defined in claim 41, in which the sleeve is open at both ends, having an unimpeded through bore.

46. The splice defined in claim 41, in which the securing means includes means for mechanically securing the cord to the sleeve such that tension applied to the cord is transmitted to the sleeve substantially uniformly throughout the cross section of the cord.

47. The splice defined claim 46, in which the securing means includes tensioned suture sections extending between opposing surfaces of the sleeve.

48. The splice defined in claim 46, in which the sleeve has opposite walls for extending along opposite sides of the cord, the securing means including several rigid pins extending between said walls.

49. The splice defined in claim 48, in which the pins have body portions for extending through the interior of the sleeve, each pin having a sharpened end portion projecting from such body portion and a peripheral groove between the body portion and the sharpened end portion for separation of the sharpened end portion from the body portion.

50. The splice defined in claim 41, in which the sleeve is formed of separate sections, each of said sections being hollow and being substantially aligned axially with and adjacent section, and said sections being joined together.

51. The splice defined in claim 41, in which the sleeve is formed of bioabsorbable material.

52. The splice defined in claim 41, in which the sleeve is impregnated or coated with an agent selected from the group consisting of agents for enhancing healing, agents for decreasing adhesion formation, and agents for deterring scar formation.

53. The splice defined in claim 41, in which the sleeve is elongated and of substantially uniform cross section throughout its length.

54. The splice defined in claim 53, in which the length of the sleeve is substantially greater than the maximum cross sectional dimension of the sleeve.

55. The splice defined in claim 41, in which the sleeve completely encircles the connective cord.

56. The splice defined in claim 41, in which the sleeve has an inner periphery having a longitudinally extending groove to allow vascular flow to the cord.

* * * * *

UNITED STATES PATENT AND TRADEMARK OFFICE
CERTIFICATE OF CORRECTION

PATENT NO.　:　6,080,192
DATED　　　:　June 27, 2000
INVENTOR(S):　G.A. Demopulos et al.

It is certified that error appears in the above-identified patent and that said Letters Patent is hereby corrected as shown below:

On the title page, item:

| | | |
|---|---|---|
| [56] col. 2 | Refs. Cited (Other Publs., Item 5) | "2:2:1213" should read --22:1213-- |
| [56] col. 2 | Refs. Cited (Other Publs., Item 5) | "augmentaion" should read --augmentation-- |
| [56] col. 2 | Refs. Cited (Other Publs., Item 13) | "cruicate" should read --cruciate-- |

UNITED STATES PATENT AND TRADEMARK OFFICE
CERTIFICATE OF CORRECTION

PATENT NO. : 6,080,192
DATED : June 27, 2000
INVENTOR(S) : G.A. Demopulos et al.

It is certified that error appears in the above-identified patent and that said Letters Patent is hereby corrected as shown below:

| | | |
|---|---|---|
| [56] col. 2 | Refs. Cited (Other Publs., Item 16) | "An in vitr" should read --An in vitro-- |
| 18 (Claim 12, | 59 line 5) | "against inner periphery" should read --against the inner periphery-- |
| 19 (Claim 15, | 5 line 3) | "axially aligned with and" should read --axially aligned with an-- |
| 22 (Claim 50, | 5 line 3) | "axially aligned with and" should read --axially aligned with an-- |

Signed and Sealed this

Eighth Day of May, 2001

Attest:

NICHOLAS P. GODICI

Attesting Officer     Acting Director of the United States Patent and Trademark Office